United States Patent
Gysling et al.

(10) Patent No.: US 7,617,716 B2
(45) Date of Patent: Nov. 17, 2009

(54) TOTAL GAS METER USING SPEED OF SOUND AND VELOCITY MEASUREMENTS

(75) Inventors: Daniel L. Gysling, Glastonbury, CT (US); Douglas H. Loose, Southington, CT (US)

(73) Assignee: CiDRA Corporate Services, Inc., Wallingford, CT (US)

( * ) Notice: Subject to any disclaimer, the term of this patent is extended or adjusted under 35 U.S.C. 154(b) by 273 days.

(21) Appl. No.: 11/762,407

(22) Filed: Jun. 13, 2007

(65) Prior Publication Data

US 2007/0234780 A1 Oct. 11, 2007

Related U.S. Application Data

(63) Continuation of application No. 11/205,899, filed on Aug. 16, 2005, now abandoned, application No. 11/762,407, and a continuation-in-part of application No. 11/500,073, filed on Aug. 7, 2006, now abandoned, which is a continuation of application No. 10/762,409, filed on Jan. 21, 2004, now Pat. No. 7,086,278.

(60) Provisional application No. 60/441,395, filed on Jan. 21, 2003, provisional application No. 60/441,652, filed on Jan. 22, 2003, provisional application No. 60/482,516, filed on Jun. 24, 2003, provisional application No. 60/601,919, filed on Aug. 16, 2004, provisional application No. 60/616,504, filed on Oct. 5, 2004.

(51) Int. Cl.
*G01N 29/00* (2006.01)
(52) U.S. Cl. .................................. 73/19.03
(58) Field of Classification Search ............... 73/61.46, 73/61.47, 861.18
See application file for complete search history.

(56) References Cited

U.S. PATENT DOCUMENTS 4,048,853 A 9/1977 Smith et al.

(Continued)

FOREIGN PATENT DOCUMENTS

EP 0484876 5/1992

(Continued)

OTHER PUBLICATIONS

U.S. Appl. No. 11/205,899, filed Aug. 16, 2005, Gysling, et al.

(Continued)

*Primary Examiner*—Hezron Williams
*Assistant Examiner*—Alex Devito

(57) ABSTRACT

An apparatus is provided for measuring total gas content of a fluid flowing through a process line. The apparatus comprises a bleed line in fluid communication with the process line for bleeding a portion of the fluid from the process line at a bleed line pressure that is lower than the process line pressure. A speed of sound propagating through the fluid in the bleed line is determined and is, in turn, used to determine a gas volume fraction of the fluid in the bleed line. In one aspect, the total gas content of the fluid flowing through the process line is calculated as a function of the gas volume fraction of the fluid in the bleed line and a velocity of the fluid in the bleed line. In another aspect, the velocity of the fluid in the bleed line is adjusted to be approximately equal to a predetermined velocity. In yet another aspect, dissolved gas in the process fluid 13 is released before the gas content measurement point by applying a high intensity ultrasonic field to the fluid 13.

25 Claims, 15 Drawing Sheets

U.S. PATENT DOCUMENTS

| | | | |
|---|---|---|---|
| 4,080,837 | A | 3/1978 | Alexander et al. |
| 4,248,085 | A | 2/1981 | Coulthard |
| 4,445,389 | A | 5/1984 | Potzick et al. |
| 4,896,540 | A | 1/1990 | Shakkottai et al. |
| 5,040,415 | A | 8/1991 | Barkhoudarian |
| 5,083,452 | A | 1/1992 | Hope |
| 5,218,197 | A | 6/1993 | Carroll |
| 5,367,911 | A | 11/1994 | Jewell et al. |
| 5,385,675 | A | 1/1995 | Vroman et al. |
| 5,398,542 | A | 3/1995 | Vasbinder |
| 5,524,475 | A | 6/1996 | Kolpak et al. |
| 5,526,844 | A | 6/1996 | Kamen et al. |
| 5,589,642 | A | 12/1996 | Agar et al. |
| 5,591,922 | A | 1/1997 | Segeral et al. |
| 5,741,980 | A | 4/1998 | Hill et al. |
| 5,770,805 | A | 6/1998 | Castel |
| 5,770,806 | A | 6/1998 | Hiismaki |
| 5,835,884 | A * | 11/1998 | Brown ................. 702/45 |
| 5,845,033 | A | 12/1998 | Berthold et al. |
| 5,948,959 | A | 9/1999 | Peloquin |
| 6,016,702 | A | 1/2000 | Maron |
| 6,151,958 | A | 11/2000 | Letton et al. |
| 6,202,494 | B1 | 3/2001 | Ricbel et al. |
| 6,354,147 | B1 | 3/2002 | Gysling et al. |
| 6,378,357 | B1 | 4/2002 | Han et al. |
| 6,435,030 | B1 | 8/2002 | Gysling et al. |
| 6,463,813 | B1 | 10/2002 | Gysling |
| 6,536,291 | B1 | 3/2003 | Gysling et al. |
| 6,550,342 | B2 | 4/2003 | Croteau et al. |
| 6,587,798 | B2 | 7/2003 | Kersey et al. |
| 6,601,458 | B1 | 8/2003 | Gysling et al. |
| 6,609,069 | B2 | 8/2003 | Gysling |
| 6,691,584 | B2 | 2/2004 | Gysling et al. |
| 6,732,575 | B2 | 5/2004 | Gysling et al. |
| 6,782,150 | B2 | 8/2004 | Davis et al. |
| 6,813,962 | B2 | 11/2004 | Gysling et al. |
| 6,837,098 | B2 | 1/2005 | Gysling et al. |
| 7,086,278 | B2 | 8/2006 | Gysling et al. |
| 2002/0123852 | A1 | 9/2002 | Gysling et al. |
| 2002/0129662 | A1 | 9/2002 | Gysling et al. |
| 2003/0136186 | A1 | 7/2003 | Gysling et al. |
| 2003/0154036 | A1 | 8/2003 | Gysling et al. |
| 2004/0016284 | A1 | 1/2004 | Gysling et al. |
| 2007/0062254 | A1 | 3/2007 | Gysling et al. |

FOREIGN PATENT DOCUMENTS

| | | |
|---|---|---|
| WO | 9314382 | 7/1993 |
| WO | 9967629 | 12/1999 |
| WO | 0246704 | 6/2002 |

OTHER PUBLICATIONS

"Noice and Vibration Control Engineering Principals and Applications", Leol. Beranek and Istvan L. Ver, A. Wiley Interscience Publication, pp. 537-541, Aug. 1992.

"Two Decades of an Array Signal Processing Research, The Parametric Approach", H. Krim and M. Viberg, IEEE Signal Processing Magazine, Jul. 1996 pp. 67-94.

"Development of an Array of Pressure Sensors with PVDF Film, Experiments in Fluids 26", Jan. 1999, Springer-Verlag.

"Vicous Attentuation of Acoustic Waves in Suspensions" by R.L. Gibson, Jr. and M.N. Toksoz, 1989 Acoustical Society of America, May 1989, pp. 1925-1934.

* cited by examiner though the fluid flowing through the bleed line; and determining the total gas content of the fluid flowing through the process line as a gas volume fraction of the fluid in the bleed line.

TOTAL GAS METER USING SPEED OF SOUND AND VELOCITY MEASUREMENTS

CROSS-REFERENCE TO RELATED APPLICATIONS

This application is a continuation of U.S. patent application Ser. No. of 11/205,899 filed Aug. 16, 2005 now abandoned which claimed the benefit of U.S. Provisional Patent Application No. 60/616,504, filed Oct. 5, 2004 and U.S. Provisional Patent Application No. 60/601,919, filed Aug. 16, 2004; and is a continuation in part of U.S. patent application Ser. No. 11/500,073 filed Aug. 7, 2006 now abandoned which is a continuation of U.S. patent application Ser. No. 10/762,409, filed on Jan. 21, 2004, now U.S. Pat. No. 7,086,278 which claimed the benefit of U.S. Provisional Patent Application No. 60/441,652 filed Jan. 22, 2003 and U.S. Provisional Patent Application No. 60/441,395 filed Jan. 21, 2003, and claimed the benefit of U.S. Provisional Patent Application No. 60/482,516 filed Jun. 24, 2003; which are incorporated herein by reference.

BACKGROUND

The present invention generally relates to an apparatus for measuring total gas in a fluid flowing in a process line.

Entrained gases are gases that exist in a gaseous form, mixed in the process fluid. For many industrial applications with small, less than ~20% gas fraction by volume, the gas is typically in the form of small bubbles contained in a liquid continuous mixture. Entrained gases exist as either free bubbles moving within the stock or as bound (or residual) air that is adhered to the fiber. In either cases, entrained gas can generally be detected by monitoring the compressibility of the mixture and correlating the compressibility to volumetric percentage of entrained gas.

Dissolved gases are dissolved within the mixture on a molecular level. While in the solution, dissolved gases pose few operation problems. Typically dissolved gases have a negligible effect on the compressibility of the mixture. Thus, dissolved gases are difficult to detect via compressibility measurements. The sum of the entrained gases and the dissolved gases is defined as the total gases contained with a process mixture.

Monitoring levels of entrained and dissolved gases (e.g., air) is desirable in many industrial processes. For example, entrained and dissolve gases in the approach system of paper making machines are often problematic, leading to a wide variety of problems, including flow line pulsations, pin-holes in the produced paper, reduced paper sheet strength, and excessive build-up of aerobic growths.

Although dissolved gases are typically not problematic while dissolved, problems arise when dissolved gases come out of a solution as a result of either decreases in pressure or increases in temperature. One example of this is in pressurized head boxes on paper machines where the pressure drop associated with spraying the pulp/water mixture on to the paper machine can cause dissolved gases to come out of the solution and form entrained gas.

Various technologies exist to monitor dissolved gases in a process line. Typically, such technologies require that a representative sample of the process fluid be expanded to atmospheric conditions to liberate the dissolved air in the fluid, and the resulting entrained air is measured either directly, as in entrained gas testers (EGTs), by weight of the de-aerated fluid, as in so-called "bird bath" arrangements, or by ultrasonic measurement. While such technologies work well for some applications, the accuracy of these technologies may be sensitive to the velocity of the fluid. More specifically, as the velocity of the fluid sample is reduced, a situation is created wherein gas velocity is appreciably faster than liquid velocity (gas/liquid slip), resulting in a discrepancy between the actual dissolved air and the measured dissolved air. Thus, there remains a need for an accurate method of measuring dissolved and total air in a process fluid.

SUMMARY OF THE INVENTION

The above described and other drawbacks and deficiencies are overcome or alleviated by an apparatus for measuring total gas content of a fluid flowing through a process line at a process line pressure, the apparatus comprising a bleed line in fluid communication with the process line for bleeding a portion of the fluid from the process line at a bleed line pressure that is lower than the process line pressure. A device determines a speed of sound propagating through the fluid flowing through the bleed line, and at least one processor: determines a gas volume fraction of the fluid in the bleed line using the speed of sound, determines the total gas content of the fluid flowing through the process line using the gas volume fraction of the fluid in the bleed line and a velocity of the fluid in the bleed line, and provides an output signal indicative of the total gas content of the fluid flowing through the process line.

In another aspect, there is provided an apparatus for measuring total gas content of a fluid flowing through a process line at a process line pressure. The apparatus comprises a bleed line in fluid communication with the process line for bleeding a portion of the fluid from the process line at a bleed line pressure that is lower than the process line pressure and at a bleed line velocity that is approximately equal to a predetermined velocity. A device determines a speed of sound propagating through the fluid flowing through the bleed line, and at least one signal processor: determines the total gas content of the fluid flowing through the process line as a gas volume fraction of the fluid in the bleed line using the speed of sound, and provides an output signal indicative of the total gas content of the fluid flowing through the process line.

In yet another aspect, a method for measuring total gas content of a fluid flowing through a process line at a process line pressure is provided. The method comprises: bleeding a portion of the fluid from the process line at a bleed line pressure that is lower than the process line pressure; determining a speed of sound propagating through the fluid flowing through the bleed line; determining a gas volume fraction of the fluid in the bleed line using the speed of sound; and determining the total gas content of the fluid flowing through the process line using the gas volume fraction of the fluid in the bleed line and a velocity of the fluid in the bleed line.

In yet another aspect, there is provided a method for measuring total gas content of a fluid flowing through a process line at a process line pressure. The method comprises: bleeding a portion of the fluid from the process line at a bleed line pressure that is lower than the process line pressure and at a bleed line velocity that is approximately equal to a predetermined velocity; determining a speed of sound propagating through the fluid flowing through the bleed line; and determining the total gas content of the fluid flowing through the process line as a gas volume fraction of the fluid in the bleed line.

BRIEF DESCRIPTION OF THE DRAWING

Referring now to the Drawing wherein like items are numbered alike in the various Figures.

DETAILED DESCRIPTION

Figure 1:
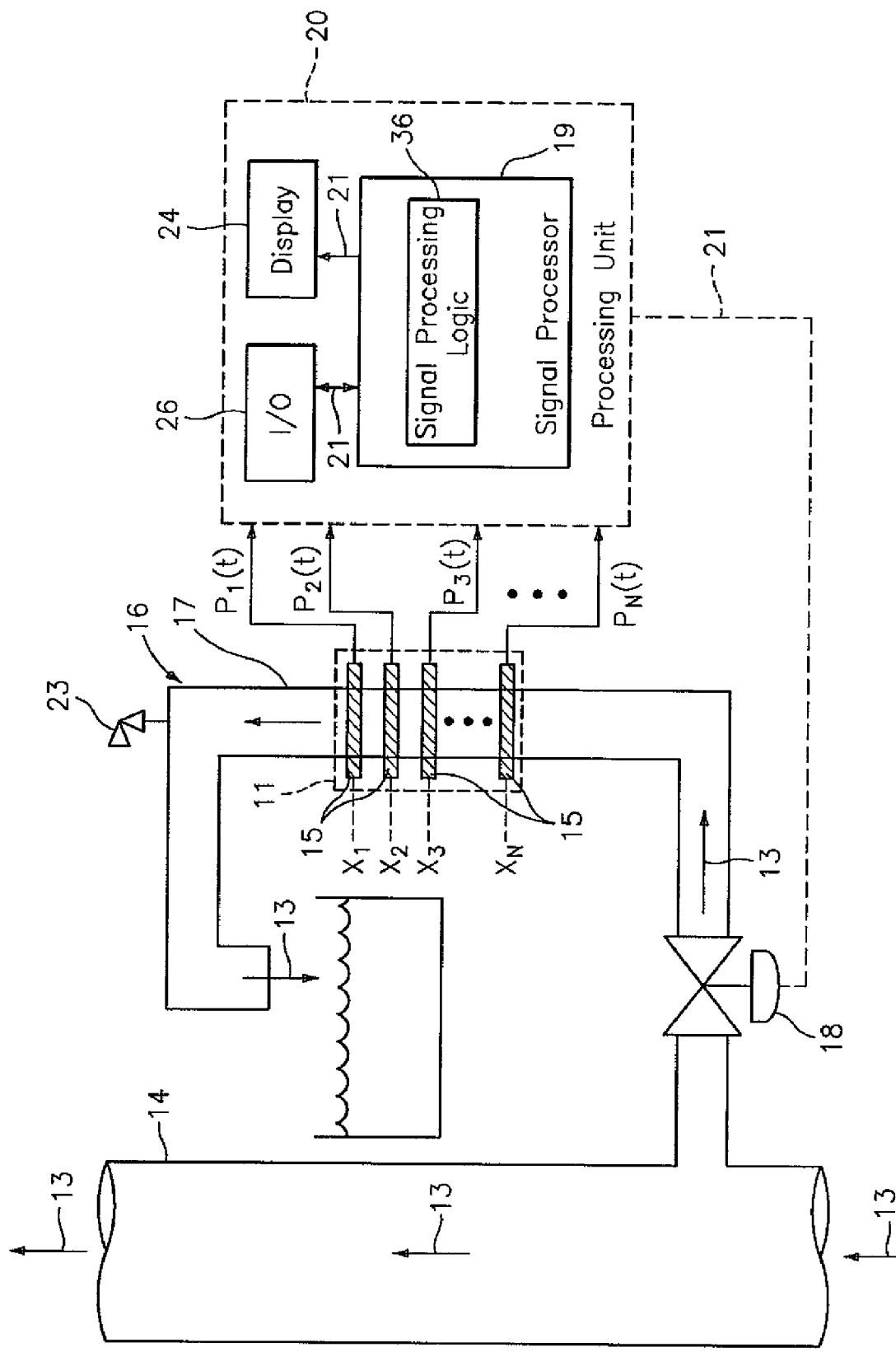
FIG. 1 is a schematic diagram of an apparatus for measuring total gas in a fluid flowing within a process line.

Referring to FIG. 1, an apparatus 10 for measuring total gas in a fluid 13 flowing within a process line 14 is shown. The apparatus 10 comprises a bleed line 16 in fluid communication with the process line 14 for bleeding a portion of the fluid 13 from the process line 14 at a bleed line pressure that is lower than the process line pressure. An array 11 of sensors 15 provides output signals $P_1(t) \ldots P_N(t)$ indicative of acoustic pressure disturbances in the fluid 13 flowing through the bleed line 16, as may be caused by acoustic waves propagating through the fluid 13 within the bleed line 16, at different axial locations $x_1 \ldots x_N$ along the bleed line 16. The signals $P_1(t) \ldots P_N(t)$ from the array 11 are used to determine a speed of sound propagating through the fluid 13 in the bleed line 16, which is in turn used to determine the total gas content of the fluid 13 in the bleed line 16. As will be discussed in further detail hereinafter, the apparatus 10 includes at least one means for accounting for the multiphase aspect of bubbly liquids to provide an accurate measurement of the total gas content of the process fluid 13. In one aspect, the total gas content of the fluid 13 flowing through the process line 14 is calculated as a function of the gas volume fraction (GVF) of the fluid 13 in the bleed line 16 and a velocity of the fluid 13 in the bleed line 16. In another aspect, the velocity of the fluid 13 in the bleed line 16 is adjusted to be approximately equal to a predetermined velocity. In yet another aspect, dissolved gas in the process fluid 13 is released before the gas content measurement point by applying a high intensity ultrasonic field to the fluid 13. Any or all of these means may be employed by the apparatus 10.

As used herein, total gas is the sum of the entrained gases and the dissolved gases contained with a fluid. Entrained gases are defined as the gas present within the fluid at process conditions (i.e. pressure and temperature in the process line 14); and dissolved gases are defined as the gas that comes out of solution when the fluid is expanded from process conditions to approximately atmospheric (ambient) pressure such as, for example, when a pulp suspension is released onto the wire of a paper machine. As used herein, a gas may be any single constituent gas (e.g., hydrogen, oxygen, etc.) or multiple constituent gas (e.g., air). As used herein, a fluid may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, gas entrained liquid or a three-phase mixture. As used herein, a line is any a duct, conduit, pipe or the like.

The bleed line 16 is in fluid communication with the process line 14 for bleeding a portion of the fluid 13 from the process line 16 at a bleed line pressure that is lower than the process line pressure. For example, the bleed line 16 pressure may be substantially atmospheric pressure (e.g. about 14.7 pounds per square inch). The array 11 is disposed on a sensing region 17 of the bleed line 16, which may be oriented vertically, such that the fluid 13 and entrained gas flow upward through the sensing region 17. The vertical orientation of the sensing region prevents stratification of the mixture 13 (i.e., separation of the gas and fluid) and ensures propagation of the entrained gas through the sensing region at a relatively constant rate.

Figure 5:
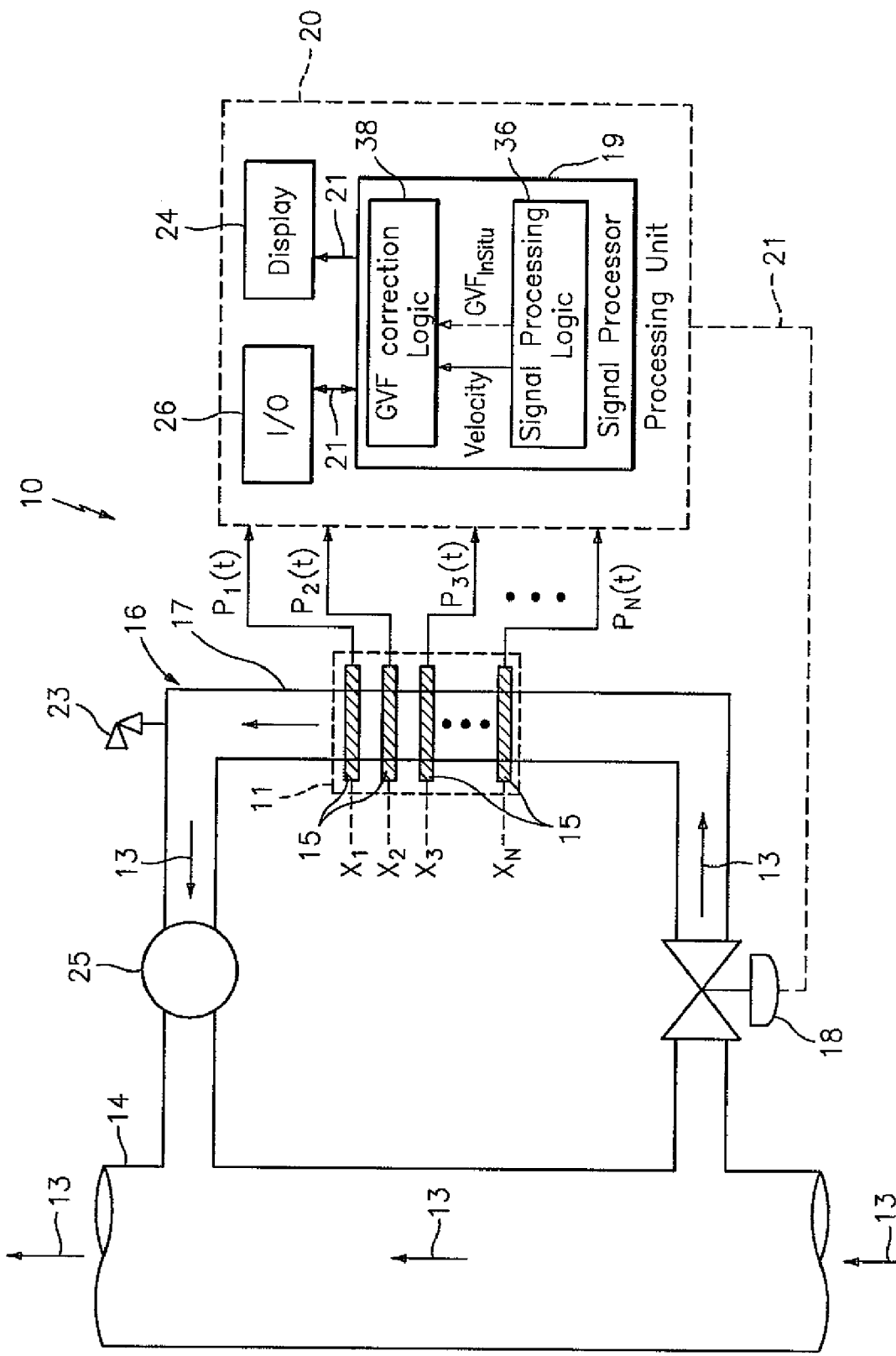
FIG. 5 is a schematic diagram of the apparatus for measuring total gas in a fluid flowing within a process line, the apparatus including a GVF correction logic.

The bleed line 16 may include one or more flow control devices 18, such as a valve, orifice, or other flow obstruction, to reduce pressure in the bleed line from that of the process line. Fluid 13 from the bleed line 16 may be provided to a tank or drain 27, or used in a different portion of the process. For example, in a paper pulp slurry application, the bleed line 16 may discharge into a white water tray. Alternatively, as depicted in FIG. 5, the bleed line 16 may also include one or more additional flow control devices 25, such as a pump, to increase fluid 13 pressure from the low pressure side of the bleed line 16 and allow the fluid 13 to be injected back into the process line 14. Referring again to FIG. 1, the low pressure side of the bleed line 16 may also include a relief valve 23 to provide a means for bringing the pressure of the fluid 13 in the sensing region 17 to ambient pressure.

The spatial array 11 includes at least two pressure sensors 15 disposed at different axial locations $x_1 \ldots x_N$ along the sensing region 17 of the bleed line 16. Each of the pressure sensors 15 provides a signal P(t) indicative of unsteady pressure within the bleed line 16 at a corresponding axial location $x_1 \ldots x_N$ of the bleed line 16. One or more signal processors 19 receives the pressure signals $P_1(t) \ldots P_N(t)$ from the pressure sensors 15 in the array 11, and applies the signals to signal processing logic 36 executed by the signal processor 19 to determine the velocity, speed of sound (SOS), gas volume fraction (GVF), total gas, and various other parameters of the fluid 13. The signal processing logic 36 is described in further detail hereinafter.

While the array 11 is shown as including four sensors 15, it is contemplated that the array 11 of pressure sensors 15 includes two or more sensors 15, each providing a pressure signal P(t) indicative of unsteady pressure within the bleed line 16 at a corresponding axial location X of the bleed line 16. For example, the array 11 may include 2, 3, 4, 5, 6, 7, 8, 9, 10, 11, 12, 13, 14, 15, 16, 17, 18, 19, 20, 21, 22, 23, or 24 pressure sensors 15. Generally, the accuracy of the measurement improves as the number of sensors 15 in the array 11 increases. The degree of accuracy provided by the greater number of sensors 15 is offset by the increase in complexity and time for computing the desired output parameter of the flow. Therefore, the number of sensors 15 used is dependent at least on the degree of accuracy desired and the desire update rate of the output parameter provided by the apparatus 10.

The signal processor 19 may be part of a larger processing unit 20. For example, the signal processor 19 may be one or more microprocessors and the processing unit 20 may be a personal computer or other general purpose computer. It is contemplated that the signal processor 19 may be any one or more analog or digital signal processing devices for executing programmed instructions, such as one or more microprocessors or application specific integrated circuits (ASICS), and may include memory for storing programmed instructions, set points, parameters, and for buffering or otherwise storing data.

The signal processor 19 may output the velocity, speed of sound (SOS), gas volume fraction (GVF), total gas, and various other parameters of the fluid 13 as a signal 21. The signal 21 may be provided to a display 24 or another input/output (I/O) device 26. The signal 21 may also be output to the flow control devices 18 and/or 25 (FIG. 5) for controlling the velocity of the fluid 13 through the bleed line 16.

The I/O device 26 may accept user input parameters 48 as may be necessary for the signal processing logic 36. The I/O device 26, display 24, and signal processor 19 unit may be mounted in a common housing, which may be attached to the array 11 by a flexible cable, wireless connection, or the like. The flexible cable may also be used to provide operating power from the processing unit 20 to the array 11 if necessary.

Figure 2:
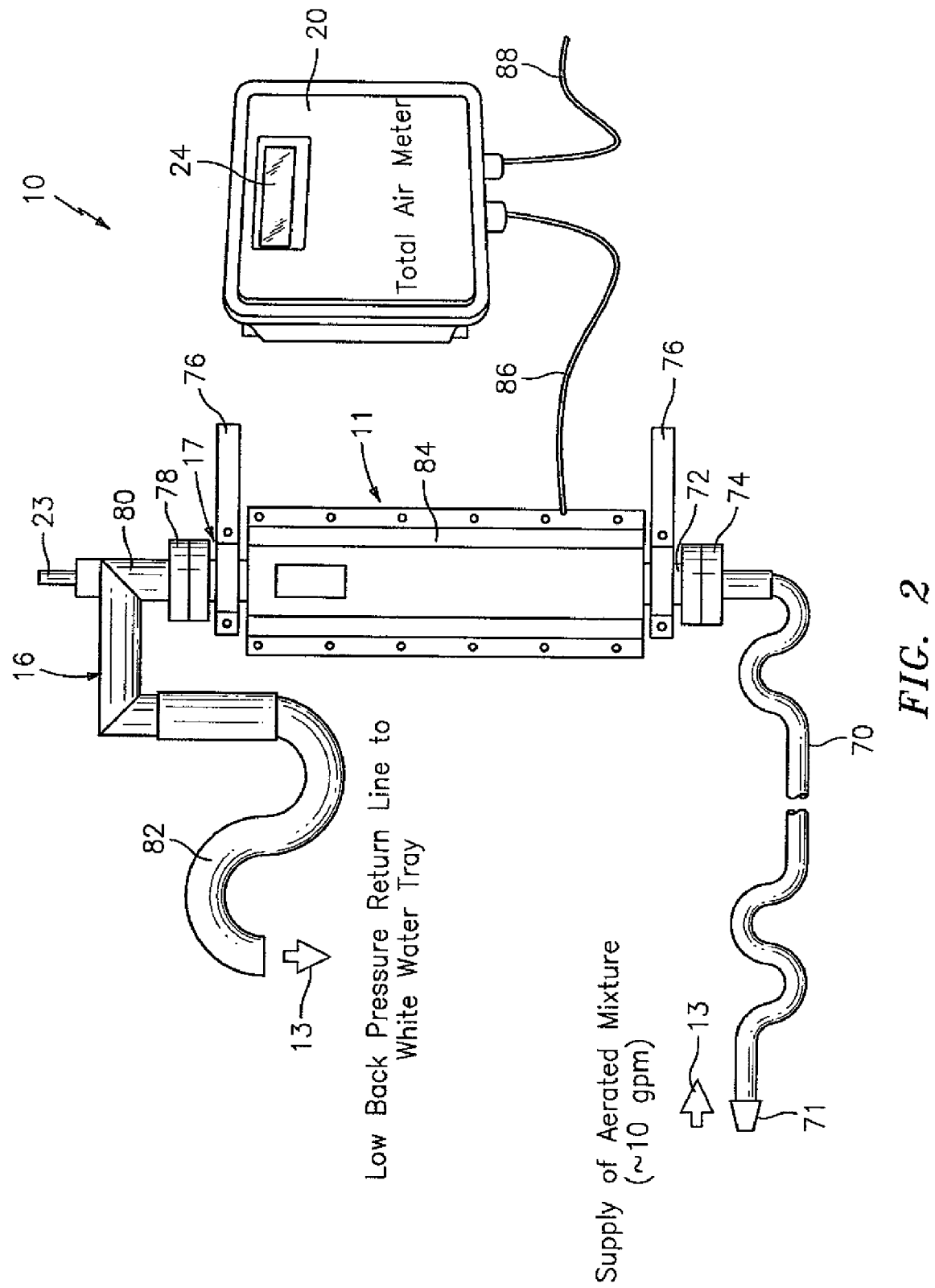
FIG. 2 is an example of the apparatus of FIG. 1 removed from the process line.

Referring to FIG. 2, an example of the apparatus 10 is shown removed from the process line 14. In this example, the bleed line 16 includes a supply hose 70 (e.g., a 2 inch EPDM (Ethylene Propylene Diene Monomer) hose) coupled to a bottom end of a pipe 72 (e.g., a 2 inch O.D. plastic pipe) by way of a flange 74. The use of a plastic pipe 72 is advantageous in that it provides more sensitivity for flow measurement by the array 11; however, other materials may be used. The supply hose 70 may be about 15 to 20 feet in length to allow sufficient time for the fluid to outgas before entering the sensing region 17. A tap 71 having a smaller diameter than the hose 70 (e.g., 1 inch inside diameter tap 71) may be secured to the end of the hose 70 to enhance outgassing in the hose 70. The pipe 72 serves as the sensing region 17 and is mounted to any convenient surface by way of mounting hardware 76 such that the longitudinal axis of the pipe 72 is vertical. A top end of the pipe 72 is coupled by way of a flange 78 (e.g., a 2 inch rotating flange) to an inverted, U-shaped pipe section 80 (e.g., 2 inch O.D. steel pipe). The relief valve 23 is in fluid communication with the pipe section 80, and a discharge hose 82 (e.g., a 2 inch EPDM hose) is fitted to a discharge end of the pipe section 80.

The array 11 is disposed around the pipe 72, and includes a housing 84 that protects the sensors 15 (FIG. 1) in the array 11. The array 11 is coupled to the processing unit 20 by a cable 86, which provides the signals $P_1(t) \ldots P_N(t)$ (FIG. 1) from the array 11 to the processing unit 20, and a cable 88 may be used to provide output signals from the processing unit 20 to a remote computer device. The array 11 and processing unit 20 may include, for example, a SONARtrac™ total air meter, which is commercially available from CiDRA Corporation of Wallingford, Conn. Advantageously, the example apparatus 10 of FIG. 2 may be shipped substantially in the assembled state shown, thus allowing the end user to install the apparatus 10 by simply mounting the pipe and processing unit, connecting the supply hose to a process line 14 (FIG. 1), and directing the return line to a low back pressure discharge (e.g., a drain, tank, white water tray, or the like).

Referring again to FIG. 1, in operation, a small amount of fluid 13 from the process line 14 is bled off the process line 14 either continuously, periodically, or upon demand, and the pressure of the fluid 13 is reduced to approximately atmospheric pressure in the bleed line 16. Once the pressure of the fluid 13 is reduced, any dissolved gas in the fluid 13 is liberated from the fluid 13 and becomes entrained gas. Thus, a measurement of the gas volume fraction (GVF) of the fluid 13 in the bleed line 16 provides the total gas measurement of the fluid 13 in the process line 14.

However, as the velocity of the fluid 13 sample is reduced in the bleed line 16, a situation can be created wherein gas velocity (relative to the pipe) is appreciably faster than liquid velocity. More specifically, in a vertical column, the buoyancy force of bubbles in the liquid phase cause the bubbles to rise faster than the liquid, a phenomenon known as slippage.

Bubbles tend to rise faster than the liquid phase of a mixture by what is often termed the "terminal velocity" of the bubble. The terminal velocity is the speed at which a bubble would rise in a liquid at rest. Since the terminal velocity represents a balance of the buoyancy force, which scales with the volume of the bubble and the drag force, which scales with the cross-sectional area of the bubble, the terminal velocity is somewhat bubble size dependent. Large bubbles rise faster than small bubbles. Despite this dependence, it is often reasonable to approximate bubble rise velocity independent of the size of the bubbles. For low consistency pulp suspensions, the bubble rise velocity tends to be approximately 0.3 to 0.8 ft/sec.

Other factors that cause the mean rise velocity of bubbles to differ from that of the liquid include the sometimes observed tendency for the bubbles to congregate near the centerline of a pipe where the velocity of the flow can be 20 to 25% greater than the volumetrically averaged flow velocity.

The combination of these effects have lead to the generally accepted model for gas velocity in a bubbly mixture in a vertical tube having the form:

$$v_{gas} = \alpha v_{liq} + v_{bubble} \tag{1}$$

where $v_{gas}$ is the velocity of gas in the sensing region 17 (relative to the sensing region 17), $v_{bubble}$ is the terminal velocity of the bubbles in the sensing region 17, $v_{liquid}$ is the velocity of the liquid in the sensing region 17 (relative to the sensing region 17), and $\alpha$ is an empirically or analytically determined parameter.

The effect of this slip between the liquid and gas phases can have a significant impact of the relationship between the actual GVF of the fluid input into the bleed line 16 ($GVF_{input}$) and the measured GVF in the bleed line 16 ($GVF_{InSitu}$). The relation between the input and in-situ gas volume fraction is given by:

$$GVF_{input} \equiv \frac{Q_{gas}}{Q_{gas} + Q_{liq}} \tag{2}$$

$$GVS_{insitu} \equiv \frac{Q_{gas}}{Q_{gas} + Q_{liq}\left(\frac{v_{gas}}{v_{liq}}\right)} \tag{3}$$

A comparison of equations 2 and 3 shows that, as the ratio between the velocity of the gas phase ($v_{gas}$) and the velocity of liquid phase ($v_{liquid}$) departs from unity, so too does the ratio between the measured GVF ($GVF_{InSitu}$) and the actual GVF ($GVF_{input}$).

Figure 3:
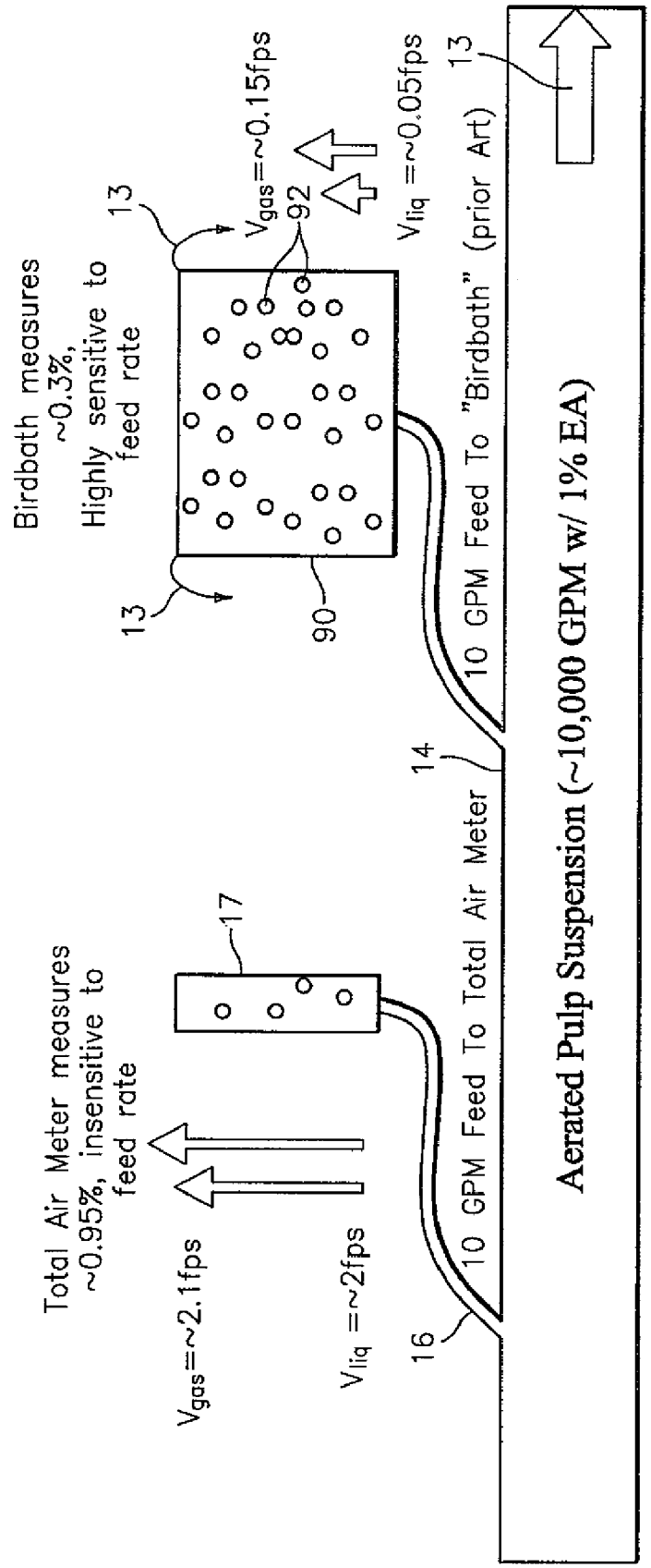
FIG. 3 is a graphic comparison of gas and liquid velocities in a prior art birdbath type meter and the apparatus of FIG. 1.
Figure 4:
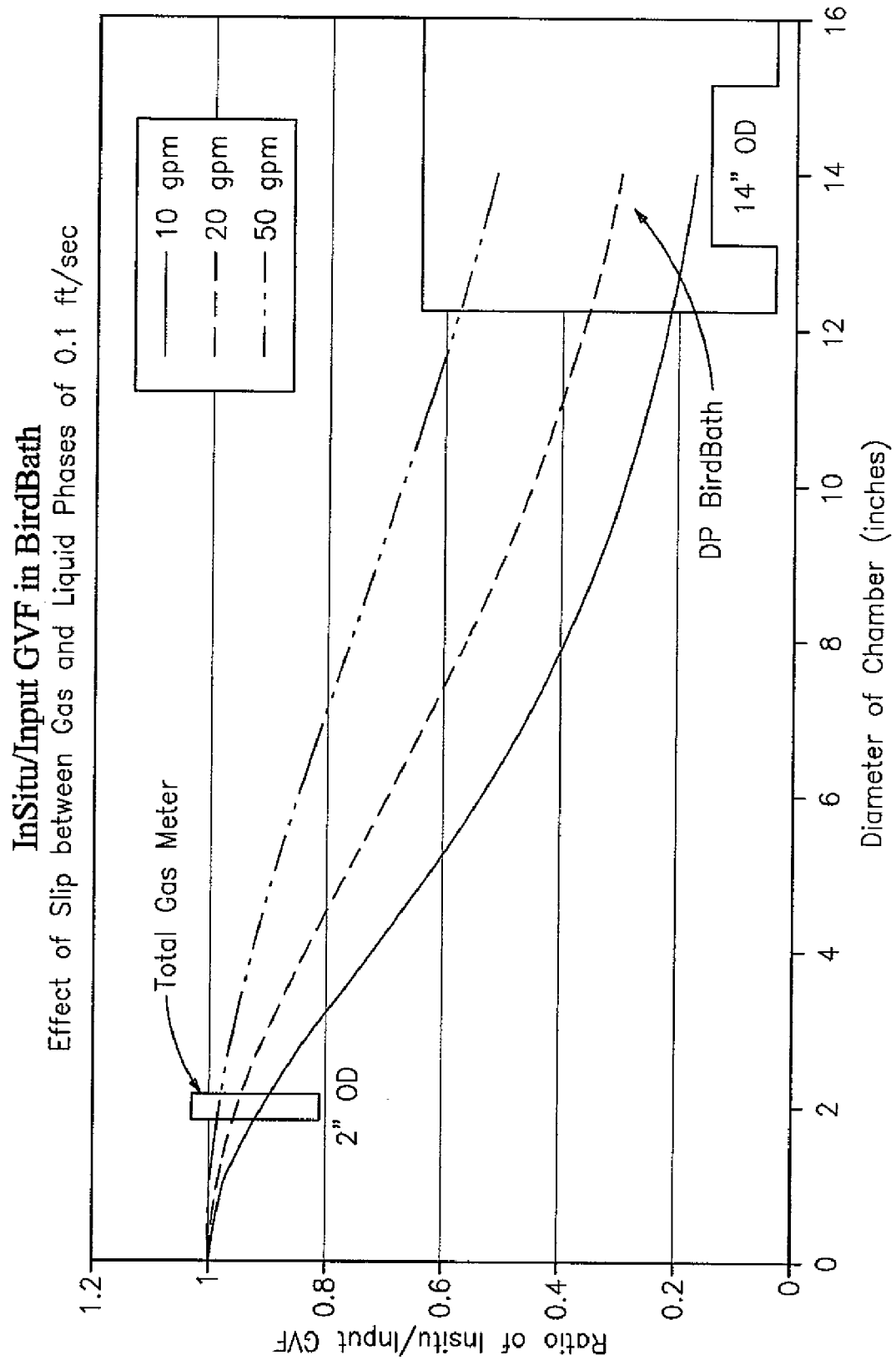
FIG. 4 is a graphic comparison of the impact of slip on a prior art birdbath type meter and the apparatus of FIG. 1.

In prior art air meters, such slippage will result in an inaccurate reading of total, entrained, and/or dissolved air. For example, in a so-called birdbath type of air meter, which is depicted in FIG. 3, aerated fluid 13 flows from the process line 14 into the bottom of a large tank 90 (e.g. a cylindrical tank 14 inches in diameter or greater), which is maintained at about atmospheric pressure. The fluid 13 flows upward in the tank 90 and overflows the edges of the tank 90 or is otherwise discharged at a predetermined tank level. As the fluid 13 flows upward through the tank 90, dissolved gas in the fluid 13 is released and becomes entrained gas bubbles 92. During this process, the weight of the volume of fluid 13 in the tank 90 is monitored. The weight of the tank 90 provides an indication of the amount of gas in the tank 90 and, therefore, the total gas in the process line 14. However, where the velocity of the gas is higher than the velocity of the liquid, this measurement may be inaccurate. For example, a 14 inch O.D. birdbath having a fluid feed of about 10 gpm will provide a liquid velocity of about 0.05 fps and a gas velocity of about 0.15 fps, which results in a ratio $GVF_{InSitu}/GVF_{input}$ of about 0.3. Moreover, the measurement is highly sensitive to the feed rate of the fluid 13 into the tank. That is, when the bubble velocity is higher than the fluid velocity, the weight reading will be greater than when the bubble velocity is approximately equal to the fluid velocity, even though the total gas in the liquid 13 from the process line 14 remains unchanged. As can be seen in FIG. 4, for example, the present inventors have determined that a fluid 13 flow rate of 10 gpm through a 14 inch O.D. birdbath results in a ratio $GVF_{InSitu}/GVF_{input}$ of about 0.5, while a fluid 13 flow rate of 50 gpm through the 14 inch O.D. birdbath results in a ratio $GVF_{InSitu}/GVF_{input}$ of about 0.18.

Referring again to FIG. 1, one means for accounting for the multiphase aspect of bubbly liquids to provide an accurate measurement of the total gas content of the process fluid 13 is to adjust the velocity of the fluid 13 in the sensing region 17 to a predetermined value. For example, the velocity of the fluid 13 in the bleed line 16 may be adjusted such that the velocity of the liquid in the sensing region 17 ($v_{liquid}$), measured as the velocity of the fluid 13 mixture, is greater than the estimated or measured terminal velocity of the bubbles in the sensing region 17 ($v_{bubble}$). Preferably the ratio $v_{liquid}/v_{bubble}$ is greater than or equal to about 4/1, and more preferably greater than or equal to about 10/1. As a result, the velocity of the gas phase and the velocity of the liquid phase will be at maintained at about unity, and the $GVF_{InSitu}$ and the $GVF_{input}$ will be approximately equal. While higher ratios are believed to provide more accurate results, it is contemplated that mechanical issues may limit the ratios that can be used for a particular application. For example, the length of inlet tubing (e.g., tube 70 of FIG. 2) needed to provide sufficient outgassing of dissolved fluids may be prohibitive for higher fluid velocities. In another example, the residency time required for sensing may be prohibitive for higher fluid velocities. Because of such mechanical limitations, it is believed that ratios greater than about 25/1 are less preferred. One will appreciate that the ratio could be higher by over coming the mechanical limitations, for example, extending the supply hose or employing ultrasonic source 94 shown in FIG. 8.

To accomplish the desired ratio $v_{liquid}/v_{bubble}$, the velocity of the fluid 13 in the sensing region 17 of the bleed line 16 may be adjusted by the selection of the size of the sensing region 17 and other portions of the bleed line 16 and/or the setting of the various flow control devices 18 and 25 in fluid communication with the bleed line 16.

For example, it has been determined that for aerated pulp suspensions, a sensing region sized to provide a liquid velocity of about 2.0 fps, provides a total gas meter that is insensitive to slippage over a flow rate range from between about 10 gpm to about 50 gpm. Thus, the sensing portion of the bleed line 17 may be designed to provide these flow parameters prior to installation of the apparatus 10. As shown in FIG. 3, for example, maintaining a fluid 13 flow of about 10 gpm through a 2 inch O.D. sensing region 17 provides a liquid velocity of about 2 fps and a gas velocity of about 2.1 fps, which results in a ratio $GVF_{InSitu}/GVF_{input}$ of about 1. Accordingly, the $GVF_{InSitu}$ measurement more accurately reflects $GVF_{input}$. In addition, as shown in FIG. 4, because the apparatus 10 may be designed to have a sensing region with a relatively small chamber diameter as compared to the prior art birdbath design (e.g., 2 inch O.D. versus 14 inch O.D.), the apparatus 10 is also less sensitive to feed rate than the birdbath type meter. For example, with a 2 inch O.D. sensing region 17, a fluid 13 flow rate of 10 gpm results in a ratio $GVF_{InSitu}/GVF_{Input}$ of about 1, while a fluid 13 flow rate of 50 gpm results in a ratio $GVF_{InSitu}/GVF_{input}$ of about 0.9. This is much more insensitive to changes in flow rate than the previously described 14 inch O.D. birdbath type meter, which resulted in $GVF_{InSitu}/GVF_{input}$ ratios of between about 0.5 to about 0.18 for the same flow rate range. Maintaining sufficiently high velocities also avoids problems associated with stratification of the fluid 13 mixture and the problems associated with either the liquid of gas phases "holding up" in the process line 14.

Referring again to FIG. 1, in lieu of, or in addition to, design modifications to the bleed line 16, the flow control device 18 may be used to adjust the velocity of the fluid 13 in the bleed line 16 after installation of the apparatus 10. It is contemplated that, such adjustments may be made manually, by field personnel, or automatically by flow control device 18 in response to signals from the signal processor 19. In the latter case, the signal processor 19 would sense the fluid 13 velocity using the array of sensors 15, as will be discussed hereinafter, and adjust the flow control device 18 in response to the sensed velocity. Alternatively, the flow control device 18 may be controlled by a device other than the signal processor 19 that senses velocity in the bleed line 16 and provides control signals to the device 18 in response to the sensed velocity.

Figure 6:
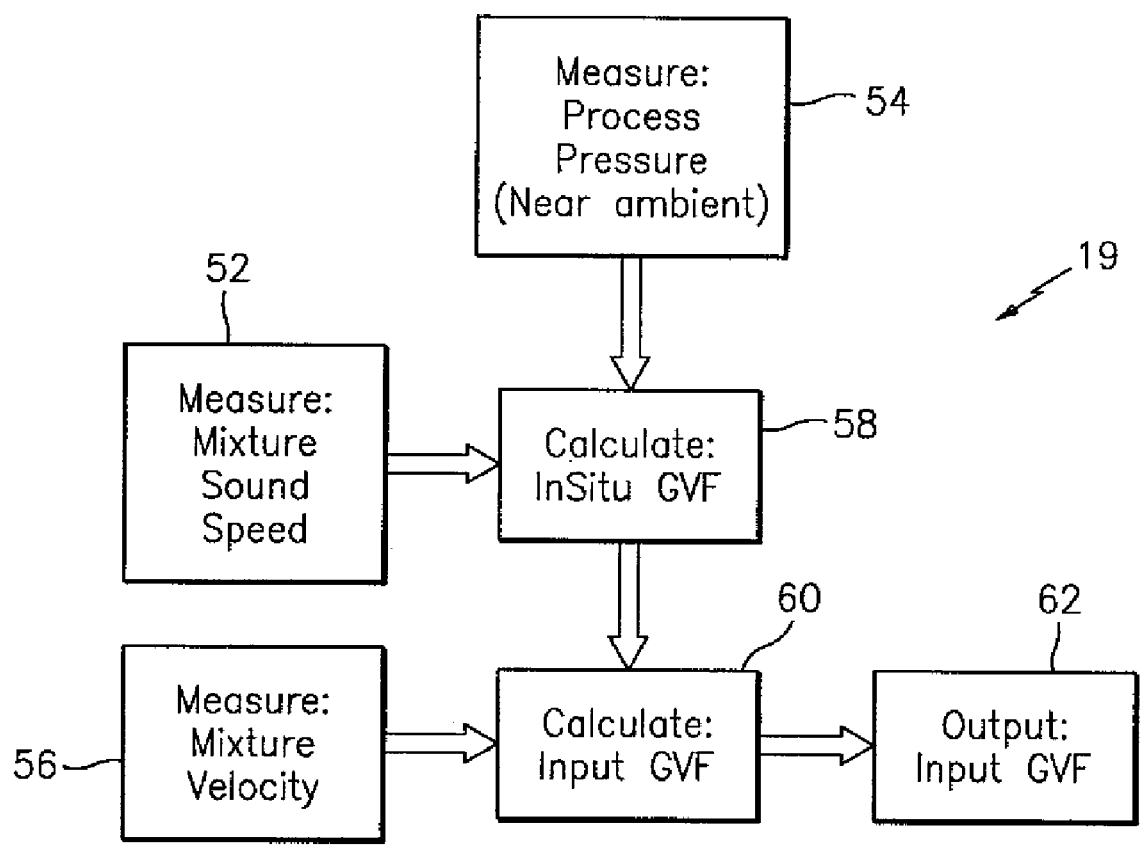
FIG. 6 is a schematic diagram of a method for measuring total gas in the fluid flowing within the process line.

FIGS. 5 and 6 depict another means for accounting for the multiphase aspect of bubbly liquids to provide an accurate measurement of the total gas content of the process fluid 13, which may be incorporated by the signal processor 19. In the embodiment of FIGS. 5 and 6, the signal processor applies a GVF correction logic 38 to the GVF determined by the signal processing logic 36. More specifically, the speed at which low frequency sound waves propagate within the fluid 13 in the sensing region 17 of the bleed line 16 is measured in the sensing region 17 by applying signals output from the array 11 (block 52 of FIG. 6) to the signal processing logic 36. Other parameters of the fluid 13 in the sensing region are also measured or estimated. For example, the pressure and temperature in the sensing region 17 is measured or estimated (block 54). Also, the volumetric flow velocity of the fluid 13 in the sensing region 17 is measured by way of the signal processing logic 36, as will be described hereinafter, or by a separate velocity sensing apparatus (block 56). The signal processor applies the signal processing logic 36 to the speed of sound (SOS) measurement, along with knowledge of the pressure and gross fluid 13 properties, to determine the in-situ GVF (block 58). The flow velocity measurement, along with knowledge of the multiphase behavior of bubbly liquids, enables the signal processor 19 to provide an accurate determination of the relationship between the sought input GVF of the fluid 13 in the process line 14 and the measured in-situ GVF of the fluid 13 within the bleed line 16, thus allowing an accurate input GVF to be determined (block 60). The calculated input GVF may then be provided by the signal processor 19 as an output signal 21 (block 62).

Rearranging the above equations (1), (2), and (3), and inserting the relationship between the gas and liquid velocity, the sought input GVF can be expressed in terms of the measured in-situ GVF and the measured liquid velocity.

$$GVF_{input} = \frac{1}{1 + \frac{1 - GVF_{insitu}}{\left(\frac{\alpha v_{liq} + v_{bubble}}{v_{liq}}\right) GVF_{insitu}}} \quad (4)$$

The relation is dependent to some degree on the slip model parameters, namely $\alpha$ and $v_{bubble}$, however, these can be derived analytically or determined empirically. Equation (4) may be applied as the GVF correction logic 38 by the signal processor 19 (block 60 of FIG. 6) to calculate the input GVF using the in-situ GVF determined by the signal processing logic 36 and the volumetric flow velocity of the fluid 13 in the sensing region 17 measured by way of the signal processing logic 36 or by a separate velocity sensing apparatus.

In this aspect of the invention, the flow velocity measurement is primarily used to account for the slip effect between the gas bubbles and the fluid in the vertical sensing region 17 of the bleed line 16. Furthermore, it has a secondary benefit of being useful in estimating flow related back pressure building up in the sensing pipe as well as correcting the measured propagation velocity of the acoustic wave for the bulk velocity motion of the fluid itself.

Figure 7:
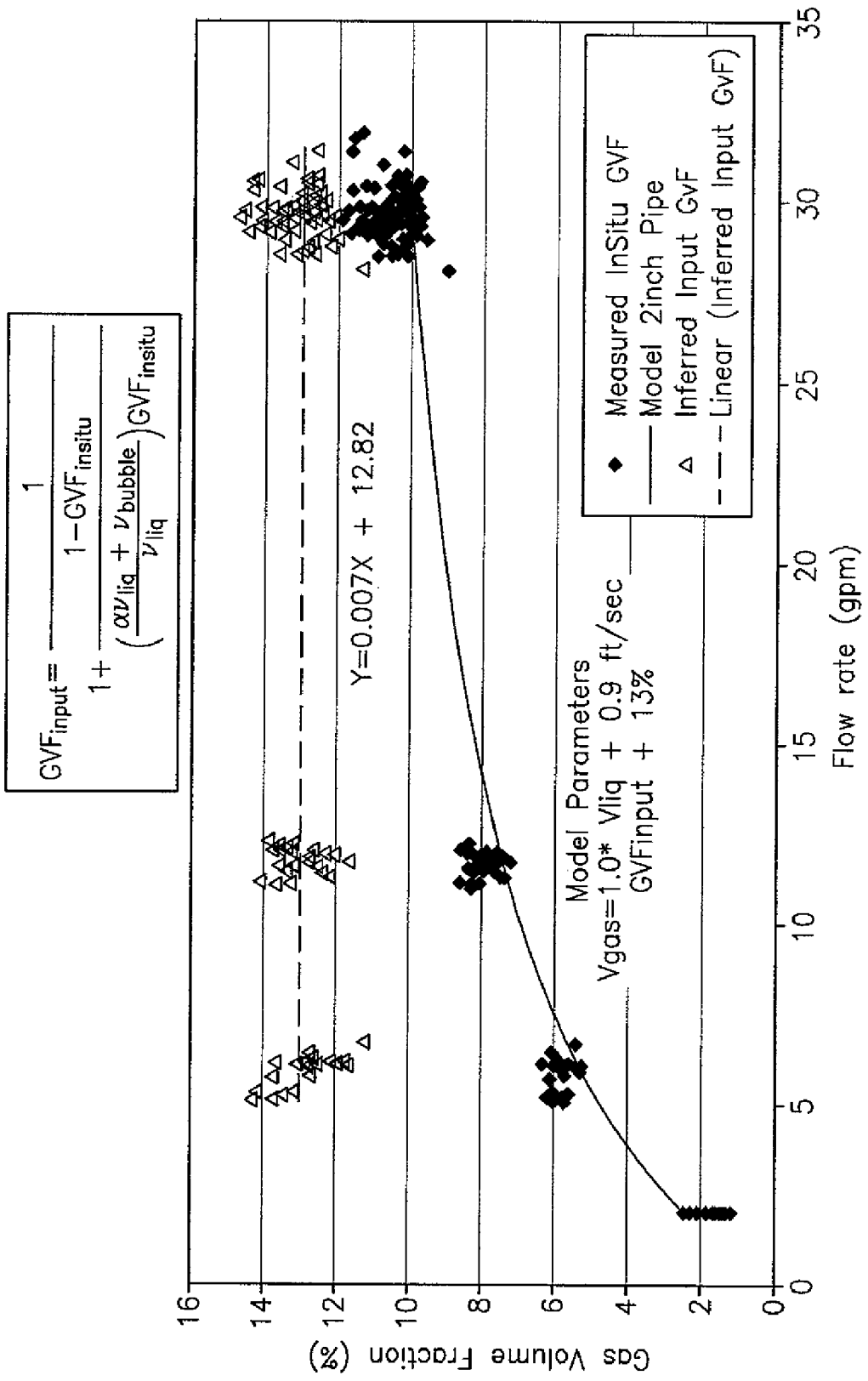
FIG. 7 is a plot depicting the effect of flow rate on the total gas measured using the method of FIG. 6.

FIG. 7 shows test data measured from a total gas meter employing the method of FIG. 6. The Total gas meter measured the velocity of the liquid and the sound speed of the mixture. The input GVF was inferred from these two measurements and a slip model as developed above. The model used $\alpha=1$ and a $v_{bubble}$ of 0.9. As shown in FIG. 7, the inferred gas volume fraction of about 13% is shown to be insensitive to the velocity of the mixture through the apparatus 10. In other words, as flow rate of the fluid 13 through the apparatus 10 changed (over a range of about 5 gpm to about 30 gpm), the measured $GVF_{input}$ remained unchanged.

Figure 8:
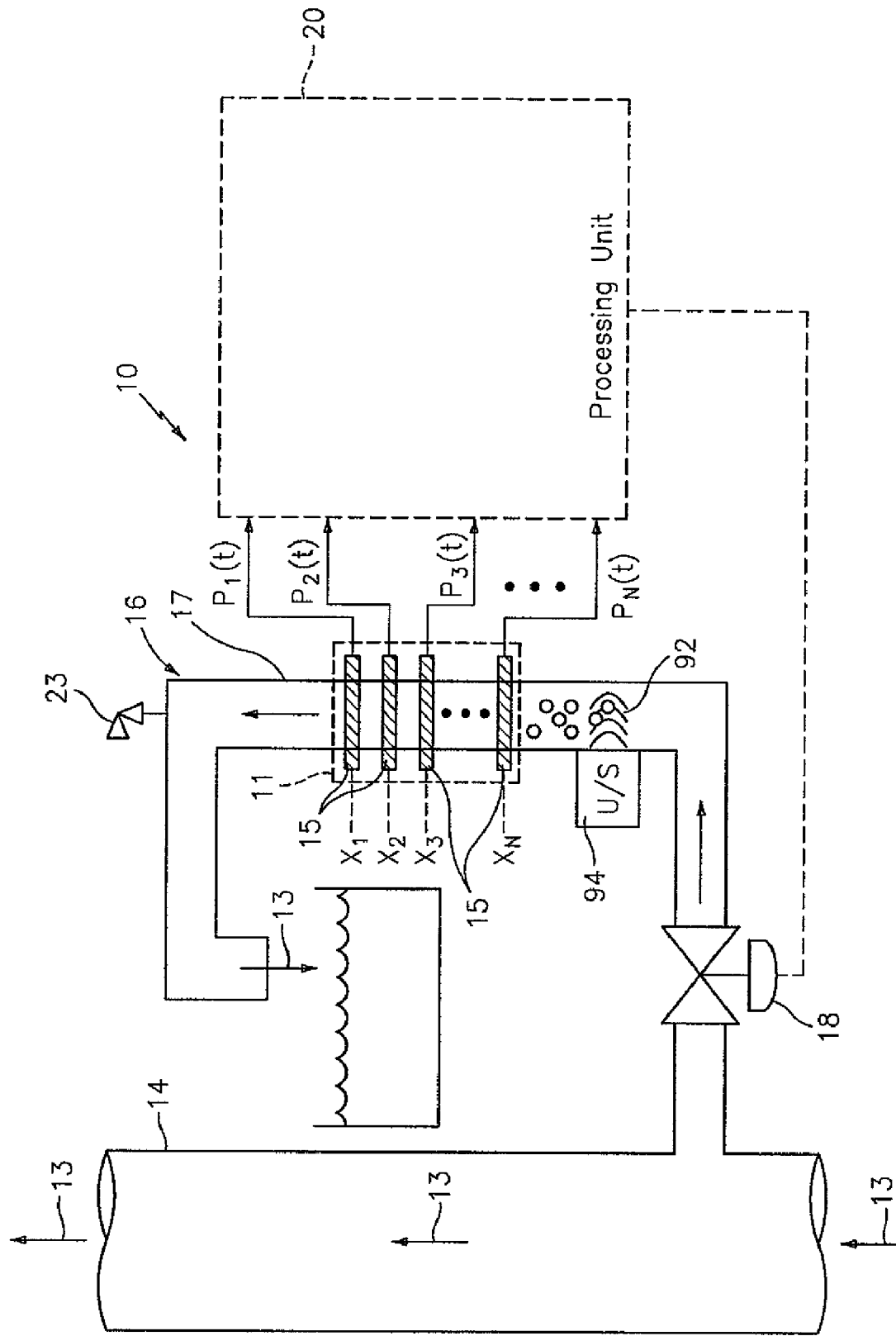
FIG. 8 is a schematic diagram of an apparatus for measuring total gas in a fluid flowing within a process line including an ultrasonic field to release dissolved gas.

FIG. 8 depicts another means for accounting for the multiphase aspect of bubbly liquids to provide an accurate measurement of the total gas content of the process fluid 13. In the embodiment of FIG. 8, the dissolved gas in the process fluid 13 is released before the gas content measurement point (e.g., the sensing region 17) by applying a high intensity ultrasonic field 92 to the fluid 13. The field 92 generates strong local pressure variations within the fluid 13 thus releasing the dissolved gas. While not wanting to be bound by theory, it is believed that the release of the gas is at least partially caused by the vibrating of the fluid 13 by the ultrasonic field 92, it is also believed that the ultrasonic field 92 causes a combining of the micro bubbles into macro bubbles minimizing the gas/liquid surface so that the gas does not dissolve back easily. Use of the ultrasonic field 92 helps to ensure that any dissolved gas is released from the liquid and, thereby, helps to provide a more accurate reading by the apparatus 10 of total air in the process line 14.

The high intensity ultrasonic field 92 can be generated by continuous wave, noise, frequency swept or pulsed ultrasound transmission applied by one or more ultrasonic sensor 94. The ultrasonic sensors 94 can be either clamped-on the bleed line 16 or directly in contact with the process fluid 13. While the embodiment of FIG. 8 depicts the use of the ultrasonic field with the apparatus 10, it is contemplated that the ultrasonic field may be used in any application where it is necessary to release dissolved gas from a liquid. For example, the ultrasonic field 92 can happen either in a batch sample volume or a continuously bypassing flow. The treatment of batch can happen in same volume as a gas measurement. Advantageously, the use of the ultrasonic field 92 provides for a fast measurement response by the apparatus 10, reduces any measurement drifts that may be caused by changes in mechanical frictions in the bleed line 16, and requires little or no maintenance.

Referring again to FIG. 1, the sensors 15 may include electrical strain gages, optical fibers and/or gratings, ported sensors, ultrasonic sensors, among others as described herein, and may be attached to the pipe 14 by adhesive, glue, epoxy, tape or other suitable attachment means to ensure suitable contact between the sensor and the pipe 14. The sensors 15 may alternatively be removable or permanently attached via known mechanical techniques such as mechanical fastener, spring loaded, clamped, clam shell arrangement, strapping or other equivalents. Alternatively, strain gages, including optical fibers and/or gratings, may be embedded in a composite pipe to form the vertical sensing region 17. If desired, for certain applications, gratings may be detached from (or strain or acoustically isolated from) the sensing region 17 if desired. It is also contemplated that any other strain sensing technique may be used to measure the variations in strain in the sensing region 17, such as highly sensitive piezoelectric, electronic or electric, strain gages attached to or embedded in the sensing region 17.

In various embodiments of the present invention, a piezoelectronic pressure transducer may be used as one or more of the pressure sensors and it may measure the unsteady (or dynamic or ac) pressure variations inside the sensing region 17 by measuring the pressure levels inside the sensing region 17. In one embodiment of the present invention, the sensors 15 comprise pressure sensors manufactured by PCB Piezotronics of Depew, N.Y. For example, in one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The sensors 15 may incorporate a built-in MOSFET microelectronic amplifier to convert the high-impedance charge output into a low-impedance voltage signal. The sensors 15 may be powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Furthermore it is contemplated that each of the sensors 15 may include a piezoelectric sensor that provides a piezoelectric material to measure the unsteady pressures of the fluid 13. The piezoelectric material, such as the polymer, polarized fluoropolymer, PVDF, measures the strain induced within the process pipe 14 due to unsteady pressure variations within the fluid 13. Strain within the sensing region 17 is transduced to an output voltage or current by the attached piezoelectric sensors 15.

The PVDF material forming each piezoelectric sensor 15 may be adhered to the outer surface of a steel strap that extends around and clamps onto the outer surface of the sensing region 17. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique are the following:

Non-intrusive flow rate measurements

Low cost

Measurement technique requires no excitation source. Ambient flow noise is used as a source.

Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals.

Higher Temperatures (140 C) (co-polymers)

Figure 9:
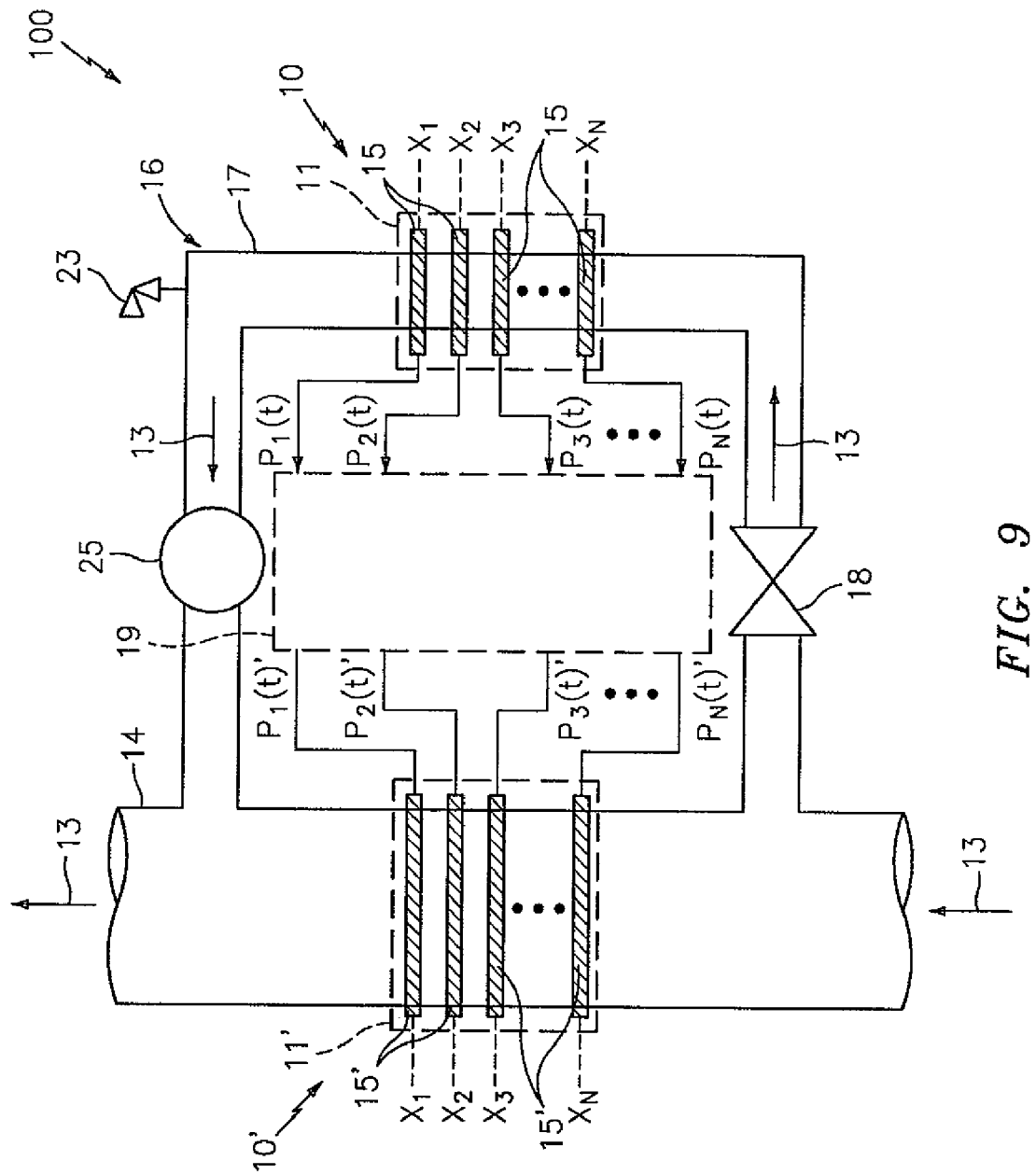
FIG. 9 is a schematic diagram of an apparatus for measuring entrained gas in the fluid flowing within the process line.

FIG. 9 depicts an apparatus 100 for measuring entrained gas in the fluid 13 flowing within the process line 14. In this embodiment, the apparatus 10 of FIG. 1 is used in conjunction with a similar apparatus 10' having its array 11' of sensors 15' arranged to sense acoustic pressure disturbances in the fluid 13 flowing through the process line 14, as may be caused by acoustic waves propagating through the fluid 13 within the process line 14. The signal processor 19 receives the pressure signals $P_1(t)' \ldots P_N(t)'$ from the pressure sensors 15' in the array 11', and applies the signals to logic 36 executed by the signal processor 19 to determine the velocity, speed of sound (SOS), gas volume fraction (GVF), and various other parameters of the fluid 13 in the process line 14. Also, the signal processor 19 receives the pressure signals $P_1(t) \ldots P_N(t)$ from the pressure sensors 15 in the array 11, and, using one or more of the above-described means for providing an accurate measurement of the total gas content of the process fluid 13 described above, applies the signals to logic 36 and 38 executed by the signal processor 19 to determine the velocity, speed of sound (SOS), input gas volume fraction ($GVF_{input}$), and various other parameters of the fluid 13 in the bleed line 16.

As described in U.S. patent application Ser. No. 10/762,409, filed Oct. 7, 2004, which is incorporated by reference herein in its entirety, the GVF determined using the pressure signals $P_1(t)' \ldots P_N(t)'$ is the GVF of entrained air in the process line 14 ($GVF_{Entrained\ Air}$), while the GVF determined using the pressure signals $P_1(t) \ldots P_N(t)$ from the bleed line is the GVF of total gas in the process line 14 ($GVF_{input}$). Accordingly, the GVF of dissolved gas in the process line 14 ($GVF_{dissolved\ gas}$) may be determined by the signal processor 19 using the equation:

$$GVF_{dissolved\ gas} = GVF_{Input} - GVF_{Entrained\ Air} \quad (5)$$

Figure 10:
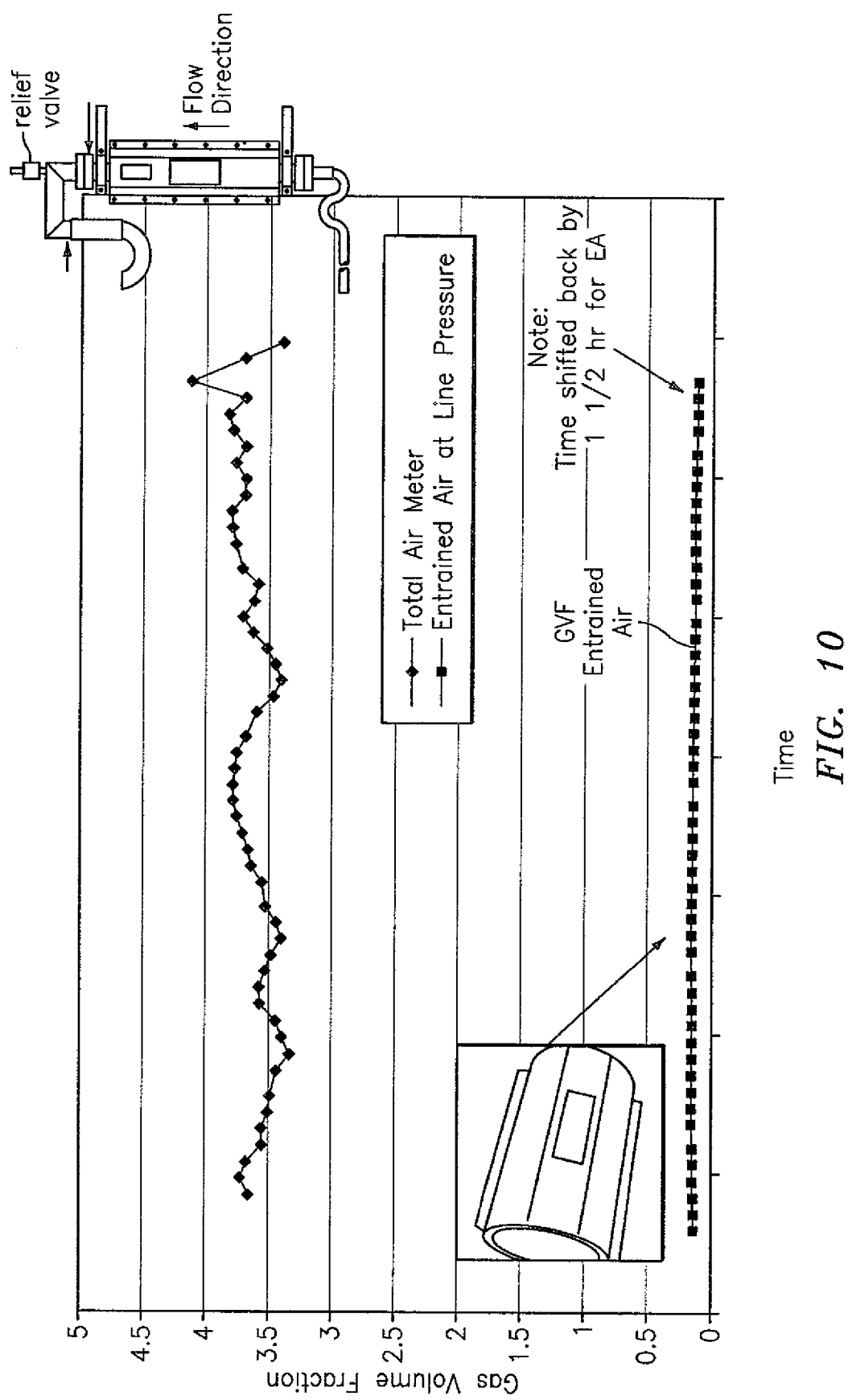
FIG. 10 is a plot depicting test data output from the apparatus of FIG. 9.

Referring to FIG. 10, a graph of test data acquired using an apparatus 100 of FIG. 9. The plot near the top of the graph of FIG. 10 depicts the total air measurement ($GVF_{Input}$) as a function of time as provided by the apparatus 10 of FIG. 9. The plot near the bottom of the graph depicts the entrained air measurement ($GVF_{Entrained\ Air}$) as a function of time provided by the apparatus 10' of FIG. 9. A comparison of these two plots reveals a difference of about 3.5% GVF between $GVF_{Input}$ and $GVF_{Entrained\ Air}$. As described with reference to equation (5) above, this difference represents the amount of dissolved gas in the process fluid ($GVF_{dissolved\ gas}$). Thus, the apparatus 100 has shown the ability to accurately provide dissolved gas measurements.

Signal Processing Logic—Entrained Gas Measurement

The example described herein uses the speed at which sound propagates within a conduit to measure entrained gas in the fluid. The apparatus measures the speed at which acoustic wave propagating in the process piping to determine the total gas in the process line 14. The acoustic wave can be generated by a pump or other device disposed in the piping system, or generated simply by the mixture/fluid flowing through the process line 14 and bleed line 16, all of which provide a passive acoustic source. Alternatively, the apparatus 10 may include an active acoustic source that injects an acoustic wave into the flow such as by compressing, vibrating and/or tapping the process line 14 or bleed line 16, to name a few examples.

This approach may be used with any technique that measures the sound speed of the fluid. However, it is particularly synergistic with sonar based volumetric flow meters such as described in U.S. patent application Ser. No. 10/007,736, in that the sound speed measurement, and thus gas volume fraction measurement, can be accomplished using the same hardware as that required for the volumetric flow measurement. It should be noted, however, that the gas volume fraction (GVF) measurement could be performed independently of a volumetric flow measurement, and would have utility as an important process measurement in isolation or in conjunction with other process measurements.

Firstly, the sound speed may be measured as described in aforementioned U.S. patent application Ser. No. 09/344,094, Ser. No. 10/007,749, U.S. patent application Ser. No. 10/349,716 filed Jan. 23, 2003 and/or U.S. patent application Ser. No. 10/376,427 filed Feb. 26, 2003, all incorporated herein by reference, using an array of unsteady pressure transducers. For a two component mixture, utilizing relations described in U.S. patent application Ser. No. 09/344,094 and/or Ser. No. 10/007,749, knowledge of the density and sound speed of the two components and the compliance properties of the conduit or pipe, the measured sound speed can be used to determine the volumetric phase fraction of the two components.

Figure 11:
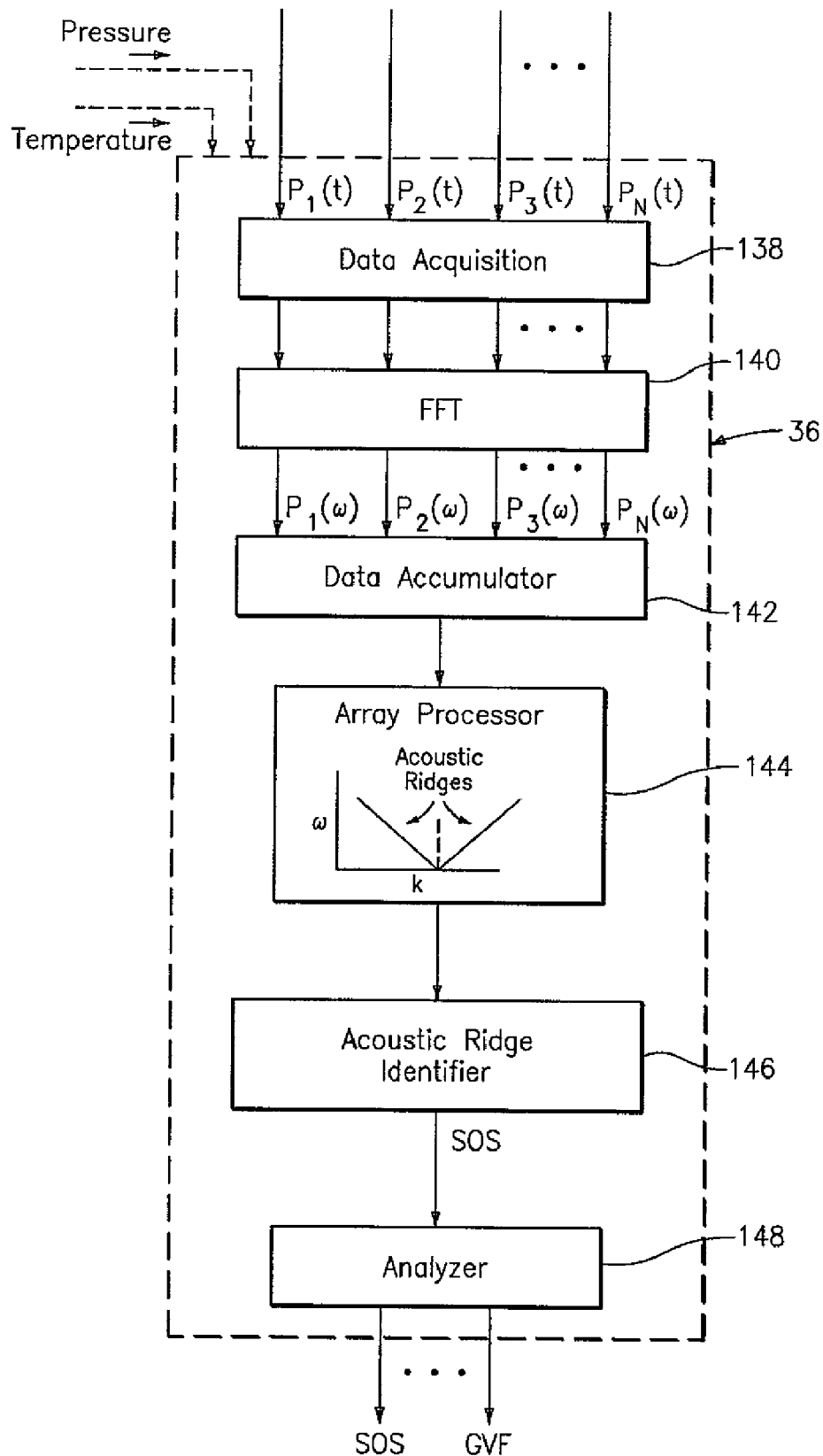
FIG. 11 is a schematic diagram of signal processing logic.

As previously described, the array 11 of at least two sensors 15 located at two at least two locations $x_1, x_2$ axially along the sensing region 17 (and, in the embodiment of FIG. 9, the process line 14) sense respective stochastic signals propagating between the sensors within the line at their respective locations. Each sensor 15 provides a signal indicating an unsteady pressure at the location of each sensor 15, at each instant in a series of sampling instants. One will appreciate that the sensor array 11 may include more than two pressure sensors 15 distributed at locations $x_1 \ldots x_N$. The pressure generated by the acoustic pressure disturbances (e.g., acoustic waves) may be measured through strained-based sensors and/or pressure sensors. The sensors 15 provide analog pressure time-varying signals $P_1(t), P_2(t), P_3(t), \ldots P_N(t)$ to the signal processing logic 36. Referring to FIG. 11, the logic 36 processes the signals $P_1(t), P_2(t), P_3(t), \ldots P_N(t)$ from the sensors 15 to first provide output signals indicative of the speed of sound propagating through the fluid (process flow) 13, and subsequently, provide output signals in response to pressure disturbances generated by acoustic waves propagating through the process flow 13, such as velocity, Mach number and volumetric flow rate of the process flow 13.

The signal processor 19 receives the pressure signals from the array 11 of sensors 15. A data acquisition unit 138 digitizes the pressure signals $P_1(t) \ldots P_N(t)$ associated with the acoustic waves 122 propagating through the pipe 14. An FFT logic 140 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals.

A data accumulator 142 accumulates the frequency signals $P_1(\omega) \ldots P_N(\omega)$ over a sampling interval, and provides the data to an array processor 144, which performs a spatial-temporal (two-dimensional) transform of the sensor data, from the xt domain to the k-$\omega$ domain, and then calculates the power in the k-$\omega$ plane, as represented by a k-$\omega$ plot.

To calculate the power in the k-$\omega$ plane, as represented by a k-$\omega$ plot (see FIG. 12) of either the signals or the differenced signals, the array processor 144 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of arrays of sensor units 15.

Figure 12:
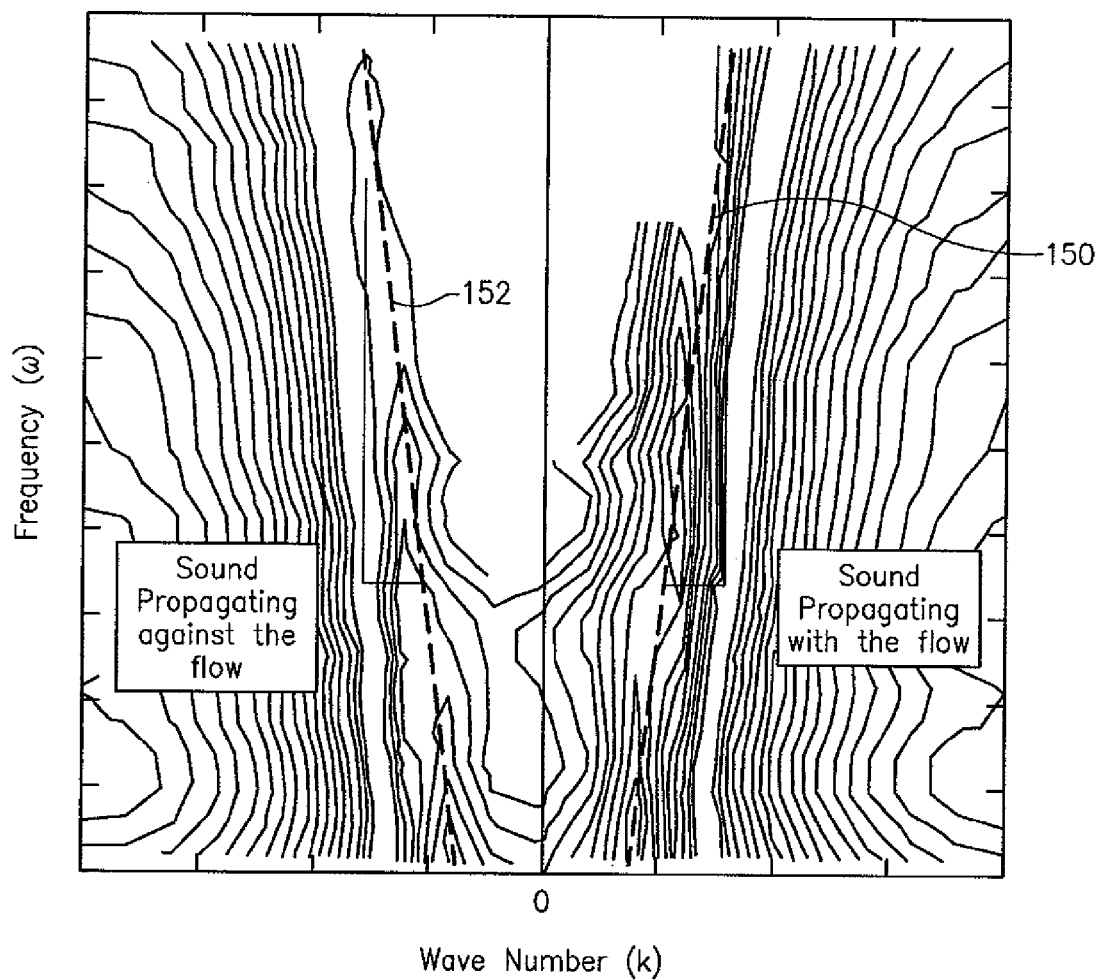
FIG. 12 is a k-ω plot of data processed by the signal processing logic that illustrates slope of the acoustic ridges.

In the case of suitable acoustic waves 122 being present in both axial directions, the power in the k-$\omega$ plane shown in a k-$\omega$ plot of FIG. 12 so determined will exhibit a structure that is called an acoustic ridge 150, 152 in both the left and right planes of the plot, wherein one of the acoustic ridges 150 is indicative of the speed of sound traveling in one axial direction and the other acoustic ridge 152 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-$\omega$ pairs to appear more or less along a line 150, 152 with some slope, the slope indicating the speed of sound.

The power in the k-$\omega$ plane so determined is then provided to an acoustic ridge identifier 146, which uses one or another feature extraction method to determine the location and orientation (slope) of any acoustic ridge present in the left and right k-$\omega$ plane. The velocity may be determined by using the slope of one of the two acoustic ridges 150, 152 or averaging the slopes of the acoustic ridges 150, 152.

Finally, information including the acoustic ridge orientation (slope) is used by an analyzer 148 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained gas within the flow.

The array processor 144 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the process flow 13 is using array processing techniques to define an acoustic ridge in the k-$\omega$ plane as shown in FIG. 12. The slope of the acoustic ridge is indicative of the speed of sound propagating through the process flow 13. The speed of sound (SOS) is determined by applying sonar arraying processing techniques to determine the speed at which the one dimensional acoustic waves propagate past the axial array of unsteady pressure measurements distributed along the sensing region 17.

The logic 36 of the present embodiment measures the speed of sound (SOS) of one-dimensional sound waves propagating through the process flow 13 to determine the gas volume fraction of the process flow 13. It is known that sound propagates through various mediums at various speeds in such fields as SONAR and RADAR fields. The speed of sound propagating through the sensing region 17 and process flow 13 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 15 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 148 of the logic 36 provides output parameters 21 indicative of characteristics of the process flow 13 that are related to the measured speed of sound (SOS) propagating through the process flow 13. For example, to determine the gas volume fraction (or phase fraction), the analyzer 148 assumes a nearly isothermal condition for the process flow 13. As such the gas volume fraction or the void fraction is related to the speed of sound by the following quadratic equation:

$$Ax^2+Bx+C=0$$

wherein x is the speed of sound, $A=1+rg/rl^*(K_{eff}/P-1)-K_{eff}/P$, $B=K_{eff}/P-2+rg/rl$; $C=1-K_{eff}/rl^*a_{meas}{}^2$); Rg=gas density, rl=liquid density, $K_{eff}$=effective K (modulus of the liquid and pipewall), P=pressure, and $a_{meas}$=measured speed of sound.

Effectively:

$$\text{Gas Volume Fraction (GVF)} = (-B+\sqrt{B^2-4^*A^*C})/(2^*A)$$

Alternatively, the sound speed of a mixture can be related to volumetric phase fraction ($\phi_i$) of the components and the sound speed (a) and densities ($\rho$) of the component through the Wood equation.

$$\frac{1}{\rho_{mix} a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves propagating within a process flow 13 contained within a pipe (e.g., sensing region 17) exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{1/a_{mix\infty}^2 + \rho_{mix}\frac{2R}{Et}}} \quad (6)$$

The mixing rule essentially states that the compressibility of a process flow ($1/(\rho a^2)$) is the volumetrically-weighted average of the compressibilities of the components. For a process flow 13 consisting of a gas/liquid mixture at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas.

Note: "vacuum backed" as used herein refers to a situation in which the fluid surrounding the pipe externally has negligible acoustic impedance compared to that of the fluid internal to the pipe. For example, meter containing a typical water and pulp slurry immersed in air at standard atmospheric conditions satisfies this condition and can be considered "vacuum-backed".

For paper and pulp slurries, the conditions are such that for slurries with non-negligible amounts of entrained gas, say <0.01%, the compliance of standard industrial piping (Schedule 10 or 40 steel pipe) is typically negligible compared to that of the entrained gas.

Figure 13:
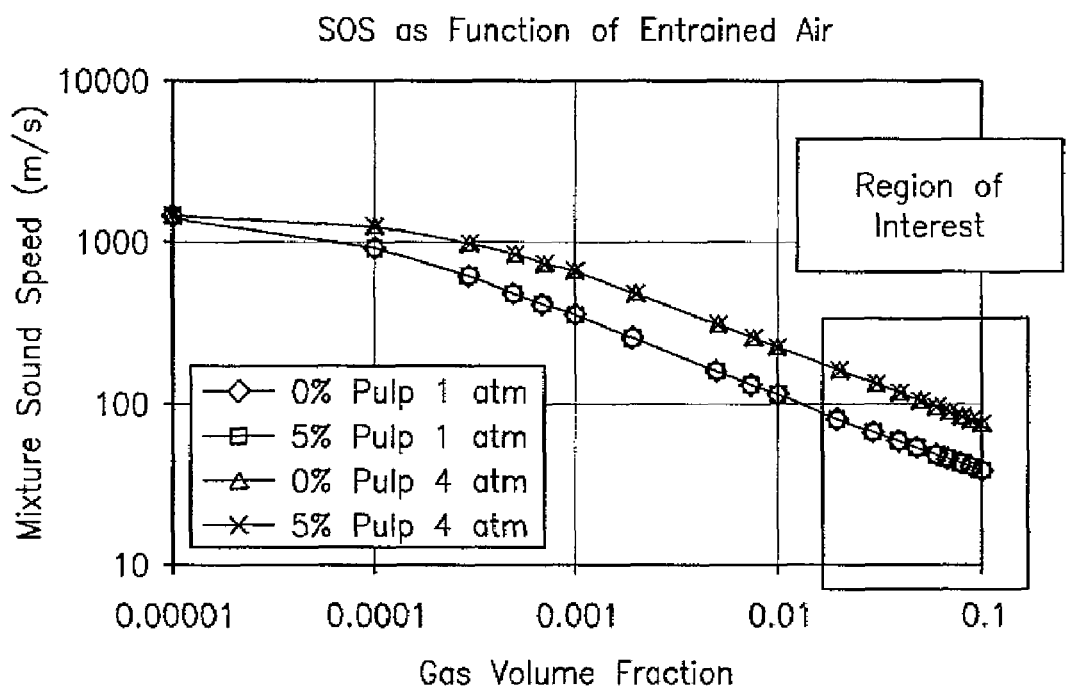
FIG. 13 is a graph of a gas volume fraction (GVF) between 0.00001 and 0.1 versus a mixture sound speed in meters per sec (m/s).
Figure 14:
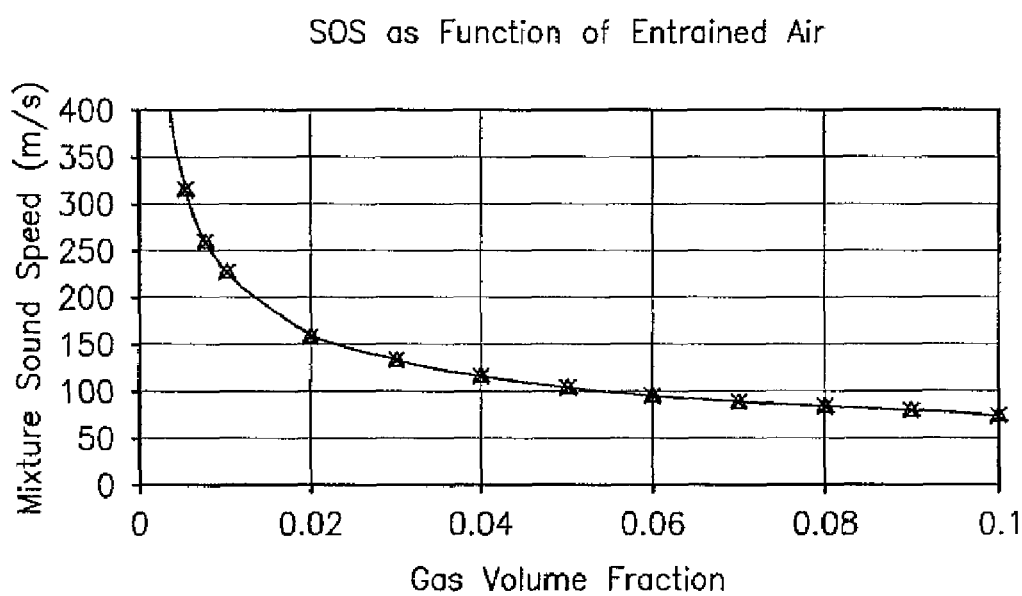
FIG. 14 is a graph of a gas volume fraction (GVF) between 0.0 and 0.1 versus a mixture sound speed in meters per sec.

FIGS. 13 and 14 show the relationship between sound speed and entrained gas for slurries with pulp contents representative of the range used in the paper and pulp industry. Referring to FIG. 13, two slurry consistencies are shown; representing the lower limit, a pure water mixture is considered, and representing the higher end of consistencies, a 5% pulp/95% water slurry is considered. Since the effect of entrained gas on the sound speed of the mixture is highly sensitive to the compressibility of the entrained gas, the effect of the entrained gas is examined at two pressures, one at ambient representing the lower limit of pressure, and one at 4 atmospheres representing a typical line pressure in a paper process. As shown, the consistency of the liquid slurry, i.e., the pulp content, has little effect on the relationship between entrained gas volume fraction and mixture sound speed. This indicates that an entrained gas measurement could be accurately performed, within 0.01% or so, with little or no knowledge of the consistency of the slurry. The chart does show a strong dependence on line pressure. Physically, this effect is linked to the compressibility of the air, and thus, this indicates that reasonable estimates of line pressure and temperature would be required to accurately interpret mixture sound speed in terms of entrained gas volume fraction.

FIG. 13 also shows that for the region of interest, from roughly 1% entrained gas to roughly 5% entrained gas, mixture sound speeds ($a_{mix}$) are quite low compared to the liquid-only sound speeds. In the example shown above, the sound speed of the pure water and the 5% pulp slurry were calculated, based on reasonable estimates of the constituent densities and compressibilities, to be 1524 m/s and 1541 m/s, respectively. The sound speed of these mixtures with 1% to 5% entrained gas at typical operating pressure (1 atm to 4 atms) are on the order of 100 m/sec. The implication of these low sound speeds is that the mixture sound speed could be accurately determined with an array of sensors, i.e. using the methodology described in aforementioned U.S. patent application Ser. No. 09/344,094, and/or Ser. No. 10/007,749, with an aperture that is similar, or identical, to an array of sensors that would be suitable to determine the convection velocity, using the methodology described in aforementioned U.S. patent application Ser. No. 10/007,736, which is incorporated herein by reference.

Based on the above discussion, one may use a short length scale aperture to measure the sound speed.

The characteristic acoustic length scale is: $\lambda = c/f$; where c is the speed of sound in a mixture, f is frequency and $\lambda$ is wavelength. If Aperture=L and if L/$\lambda$ is approx. constant. Then $$L\text{water}/\lambda\text{water} = L\text{water}^*f/C_{water} \approx L_{GVF}^*f/c_{GVF}$$

Therefore:

$L_{GVF} = L\text{water}(C_{GVF}/C_{water})$; where GVF is gas volume fraction.

Thus for SOS of water (Cwater=5,000 ft/sec), and SOS of the Gas volume fraction (C GVF=500 ft/sec) and a length aperture of L water=5 ft (which we have shown is sufficient to accurately measure the SOS of water), the length aperture for a gas volume fraction $L_{GVF}$ would be about 0.5 feet.

Note that this entrained gas or gas volume fraction measurement GVF air may be used with any flow meter or consistency meter to correct for errors introduced into a measurement by entrained gas. In particular, an electromagnetic flow meter will show an error when entrained gas exists in the mixture. The apparatus 10 may be used to correct for this error. In addition, a consistency meter will show an error when entrained gas exists in the mixture. The apparatus 10 may be used to correct for this error.

The connection between speed of sound of a two-phase mixture and phase fraction is well established for mixtures in which the wavelength of the sound is significantly larger than any inhomogenicities, i.e. bubbles, in the flow.

The mixing rule essentially states that the compressibility of a mixture ($1/(\rho a^2)$) is the volumetrically-weighted average of the compressibilities of the components. For gas/liquid mixtures at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained gas volume fraction is shown in FIG. 13.

Conversely, however, detailed knowledge of the liquid/slurry is not required for entrained gas measurement. Variations in liquid density and compressibility with changes in consistency have a negligible effect on mixture sound speed compared to the presence of entrained gas. FIG. 14 shows the mixture sound speed as a function of entrained gas volume fraction for two slurries, one with 0% wood fiber and the other with 5% wood fiber by volume. As shown, the relationship between mixture sound speed and gas volume fraction is essentially indistinguishable for the two slurries. Furthermore, mixture sound speed is shown to an excellent indicator of gas volume fraction, especially for the trace to moderate amounts of entrained gas, from 0 to 5% by volume, typically encountered in the paper and pulp industry.

Signal Processing Logic—Velocity Measurement

Figure 15:
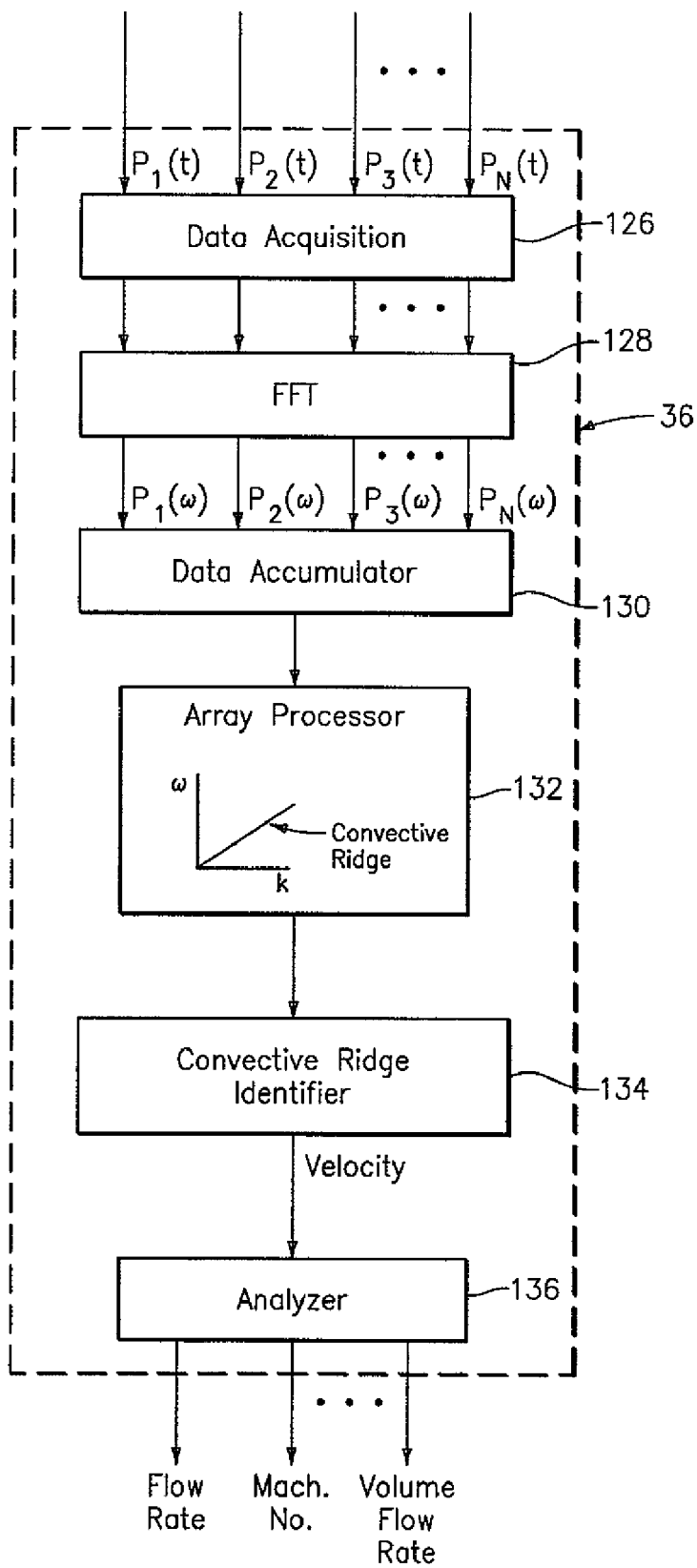
FIG. 15 is a block diagram of a flow logic used in the apparatus of the present invention.

Referring to FIG. 15, an example of flow logic 36 is shown. As previously described, each array of at least two sensors located at two locations $x_1, x_2$ axially along the pipe 72 sense respective stochastic signals propagating between the sensors within the pipe at their respective locations. Each sensor provides a signal indicating an unsteady pressure at the location of each sensor, at each instant in a series of sampling instants. One will appreciate that each sensor array may include more than two sensors distributed at locations $x_1 \ldots x_N$. The pressure generated by the convective pressure disturbances (e.g., eddies or vortical disturbances) may be measured through strained-based sensors and/or pressure sensors. The sensors provide analog pressure time-varying signals $P_1(t), P_2(t), P_3(t), P_N(t)$ to the flow logic 36.

The flow logic 36 processes the signals $P_1(t), P_2(t), P_3(t), P_N(t)$ to first provide output signals (flow parameters) indicative of the pressure disturbances that convect with the fluid (process flow) 13, and subsequently, provide output signals in response to pressure disturbances generated by convective waves propagating through the fluid 13, such as velocity, Mach number and volumetric flow rate of the process flow 13. The flow logic 36 processes the pressure signals to first provide output signals indicative of the pressure disturbances that convect with the process flow 13, and subsequently, provide output signals in response to pressure disturbances generated by convective waves propagating through the process flow 13, such as velocity, Mach number and volumetric flow rate of the process flow 13.

The flow logic 36 receives the pressure signals from the array of sensors 15. A data acquisition unit 126 (e.g., A/D converter) converts the analog signals to respective digital signals. The FFT logic 128 calculates the Fourier transform of the digitized time-based input signals $P_1(t)-P_N(t)$ and provides complex frequency domain (or frequency based) signals $P_1(\omega), P_2(\omega), P_3(\omega), P_N(\omega)$ indicative of the frequency content of the input signals. Instead of FFT's, any other technique for obtaining the frequency domain characteristics of the signals $P_1(t)-P_N(t)$, may be used. For example, the cross-spectral density and the power spectral density may be used to form a frequency domain transfer functions (or frequency response or ratios) discussed hereinafter.

One technique of determining the convection velocity of the turbulent eddies 120 within the process flow 13 is by characterizing a convective ridge of the resulting unsteady pressures using an array of sensors or other beam forming techniques, similar to that described in U.S. patent application Ser. No. and U.S. patent application Ser. No. 09/729,994, filed Dec. 4, 200, now U.S. Pat. No. 6,609,069, which are incorporated herein by reference.

A data accumulator 130 accumulates the frequency signals $P_1(\omega)-P_N(\omega)$ over a sampling interval, and provides the data to an array processor 132, which performs a spatial-temporal (two-dimensional) transform of the sensor data, from the xt domain to the k-ω domain, and then calculates the power in the k-ω plane, as represented by a k-ω plot.

The array processor 132 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=-2\pi/\lambda$ where $\lambda$ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,$$

where u is the convection velocity (flow velocity). A plot of k-ω pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 120 is distributed over a range of length scales and hence temporal frequencies.

To calculate the power in the k-ω plane, as represented by a k-ω plot (see FIG. 16) of either the signals, the array processor 132 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 15.

The present invention may use temporal and spatial filtering to precondition the signals to effectively filter out the common mode characteristics $P_{common\ mode}$ and other long wavelength (compared to the sensor spacing) characteristics in the pipe 14 by differencing adjacent sensors and retain a substantial portion of the stochastic parameter associated with the flow field and any other short wavelength (compared to the sensor spacing) low frequency stochastic parameters.

Figure 16:
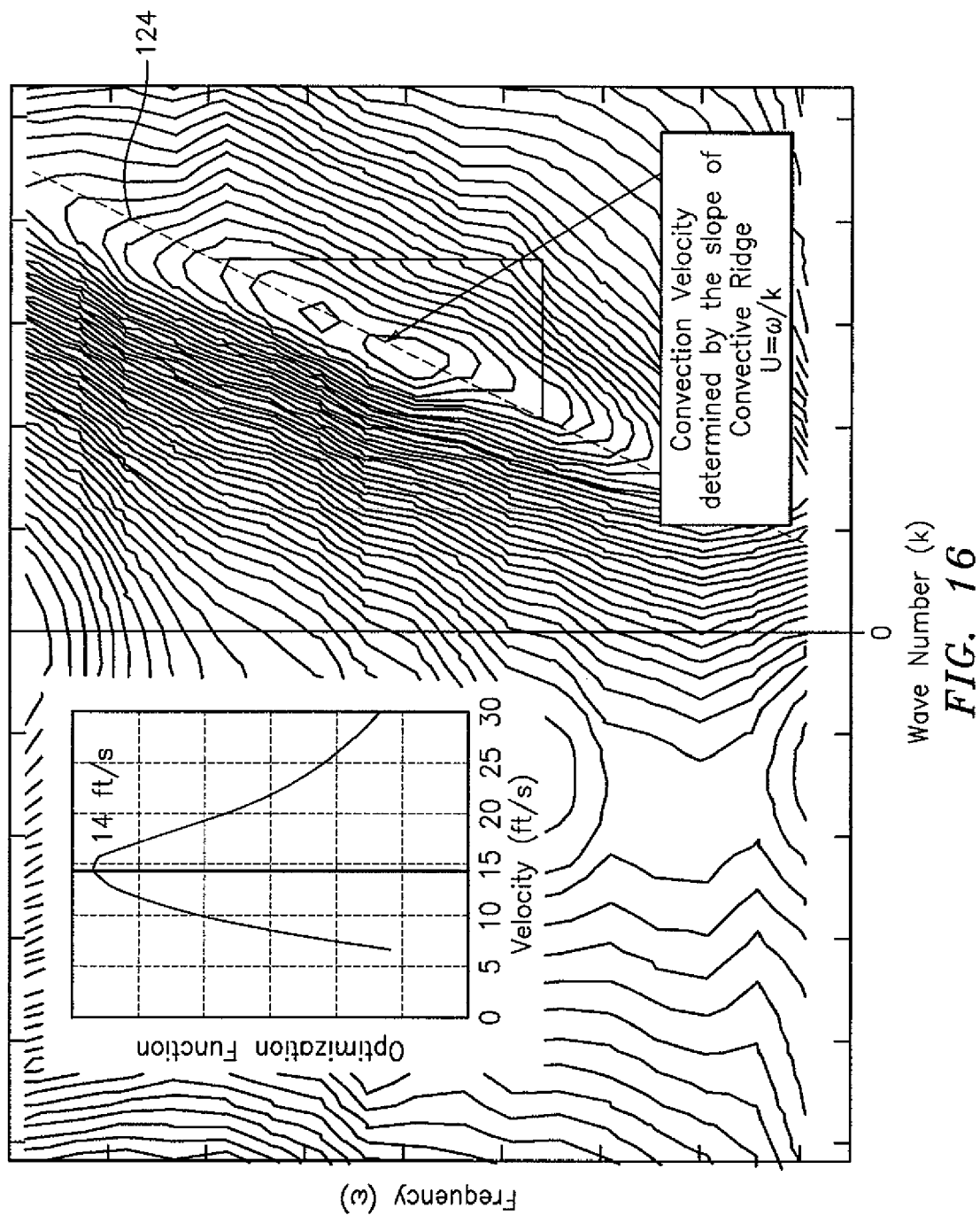
FIG. 16 is a kω plot of data processed from an apparatus embodying the present invention that illustrates slope of the convective ridge, and a plot of the optimization function of the convective ridge

In the case of suitable turbulent eddies being present, the power in the k-ω plane shown in a k-ω plot of FIG. 16 shows a convective ridge 124. The convective ridge represents the concentration of a stochastic parameter that convects with the flow and is a mathematical manifestation of the relationship between the spatial variations and temporal variations described above. Such a plot will indicate a tendency for k-ω pairs to appear more or less along a line 124 with some slope, the slope indicating the flow velocity.

Once the power in the k-ω plane is determined, a convective ridge identifier 134 uses one or another feature extraction method to determine the location and orientation (slope) of any convective ridge 124 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 134 provides information about the different trial convection velocities, information referred to generally as convective ridge information.

The analyzer 136 examines the convective ridge information including the convective ridge orientation (slope). Assuming the straight-line dispersion relation given by k=ω/u, the analyzer 136 determines the flow velocity, Mach number and/or volumetric flow, which are output as parameters. The volumetric flow is determined by multiplying the cross-sectional area of the inside of the pipe with the velocity of the process flow.

Some or all of the functions within the flow logic 36 may be implemented in software (using a microprocessor or computer) and/or firmware, or may be implemented using analog and/or digital hardware, having sufficient memory, interfaces, and capacity to perform the functions described herein.

While the present invention shows a particular meter for measuring the speed of sound propagating through the pipe and/or the velocity of the fluid flowing through the pipe to measure the total gas, the present invention contemplates that any meter or means may be used to measure the speed of sound and velocity, such as ultrasonic meters known n the art.

The apparatus 10 may provide a dual function of measuring both the gas volume fraction of the mixture and the speed of sound propagating through the mixture, which is similar to that described in U.S. patent application Ser. No. 10/766,440, filed on Jan. 27, 2004; and U.S. patent application Ser. No. 10/875,857, filed on Jun. 24, 2004, which are incorporated herein by reference.

While the apparatus 10 is described as using an array of sensors to measure the speed of sound of an acoustic wave propagating through the mixture, the scope of the invention is intended to include other ways of measuring the speed of sound either known now or developed in the future.

It should be understood that, unless stated otherwise herein, any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein without departing from the spirit and scope of the present invention.

What is claimed is:

1. An apparatus for measuring total gas content of a fluid flowing through a process line at a process line pressure, the apparatus comprising:
 a bleed line in fluid communication with the process line for bleeding a portion of the fluid from the process line at a bleed line pressure that is lower than the process line pressure;
 a device for determining a speed of sound propagating through the fluid flowing through the bleed line; and
 at least one signal processor configured to:
  determine a gas volume fraction of the fluid in the bleed line using the speed of sound,
  determine the total gas content of the fluid flowing through the process line using the gas volume fraction of the fluid in the bleed line and a velocity of the fluid in the bleed line, and
  provide an output signal indicative of the total gas content of the fluid flowing through the process line.

2. The apparatus of claim 1, wherein the total gas content of the fluid flowing through the process line is determined using the equation:

$$GVF_{input} = \frac{1}{1 + \frac{1 - GVF_{insitu}}{\left(\frac{\alpha v_{liq} + v_{bubble}}{v_{liq}}\right)GVF_{insitu}}}.$$

3. The apparatus of claim 1, wherein the at least one signal processor determines the velocity of the fluid in the bleed line using the output signals from an array of sensors.

4. The apparatus of claim 1, wherein the velocity of the fluid in the bleed line is adjusted to be approximately equal to a predetermined velocity.

5. The apparatus of claim 4, wherein the velocity of the fluid in the bleed line is adjusted by at least one of: a size of the bleed line and a flow control device in fluid communication with the bleed line.

6. The apparatus of claim 1, wherein the at least one signal processor determines an amount of dissolved gas in the fluid flowing through the process line as a difference between a gas volume fraction of the fluid flowing through the process line and the total gas content of the fluid flowing through the process line.

7. The apparatus of claim 1, wherein the device for determining the speed of sound includes:
 an array of sensors disposed at different axial locations along a length of the bleed line, the array of sensors being configured to provide an output signal indicative of acoustic pressure disturbances in the fluid flowing through the bleed line at the different axial locations.

8. An apparatus for measuring total gas content of a fluid flowing through a process line at a process line pressure, the apparatus comprising:
 a bleed line in fluid communication with the process line for bleeding a portion of the fluid from the process line at a bleed line pressure that is lower than the process line pressure and at a bleed line velocity that is approximately equal to a predetermined velocity;
a device for determining a speed of sound propagating through the fluid flowing through the bleed line; and
at least one signal processor configured to:
determine the total gas content of the fluid flowing through the process line as a gas volume fraction of the fluid in the bleed line using the speed of sound, and provide an output signal indicative of the total gas content of the fluid flowing through the process line.

9. The apparatus of claim 8, wherein the velocity of the fluid in the bleed line is adjusted by at least one of: a size of the bleed line and a flow control device in fluid communication with the bleed line.

10. The apparatus of claim 8, wherein the velocity of the fluid in the bleed line is adjusted in response to a sensed velocity in the bleed line.

11. The apparatus of claim 8, wherein the at least one signal processor determines an amount of dissolved gas in the fluid flowing through the process line as a difference between a gas volume fraction of the fluid flowing through the process line and the total gas content of the fluid flowing through the process line.

12. The apparatus of claim 8, wherein the device for determining the speed of sound includes:
an array of sensors disposed at different axial locations along a length of the bleed line, the array of sensors being configured to provide an output signal indicative of acoustic pressure disturbances in the fluid flowing through the bleed line at the different axial locations.

13. The apparatus of claim 8, wherein the predetermined velocity is at least five times greater than an estimated bubble velocity.

14. A method for measuring total gas content of a fluid flowing through a process line at a process line pressure, the method comprising:
bleeding a portion of the fluid from the process line at a bleed line pressure that is lower than the process line pressure;
determining a speed of sound propagating through the fluid flowing through the bleed line;
determining a gas volume fraction of the fluid in the bleed line using the speed of sound; and
determining the total gas content of the fluid flowing through the process line using the gas volume fraction of the fluid in the bleed line and a velocity of the fluid in the bleed line.

15. The method of claim 14, wherein the total gas content of the fluid flowing through the process line is determined using the equation:

$$GVF_{input} = \frac{1}{1 + \frac{1 - GVF_{insitu}}{\left(\frac{\alpha v_{liq} + v_{bubble}}{v_{liq}}\right) GVF_{insitu}}}.$$

16. The method of claim 14, further comprising:
sensing acoustic pressure disturbances in the fluid flowing through the bleed line at different axial locations along the bleed line to provide signals indicative of the sensed acoustic pressure disturbances; and
using the signals indicative of the sensed acoustic pressure disturbances to determine the speed of sound propagating through the fluid flowing through the bleed line.

17. The method of claim 16, further comprising:
determining the velocity of the fluid in the bleed line using the signals indicative of the sensed acoustic pressure disturbances.

18. The method of claim 14, further comprising:
adjusting the velocity of the fluid in the bleed line to be approximately equal to a predetermined velocity.

19. The method of claim 14, further comprising:
determining an amount of dissolved gas in the fluid flowing through the process line as a difference between a gas volume fraction of the fluid flowing through the process line and the total gas content of the fluid flowing through the process line.

20. A method for measuring total gas content of a fluid flowing through a process line at a process line pressure, the method comprising:
bleeding a portion of the fluid from the process line at a bleed line pressure that is lower than the process line pressure and at a bleed line velocity that is approximately equal to a predetermined velocity;
determining a speed of sound propagating through the fluid flowing through the bleed line; and
determining the total gas content of the fluid flowing through the process line as a gas volume fraction of the fluid in the bleed line.

21. The method of claim 20, wherein the velocity of the fluid in the bleed line is adjusted by at least one of: a size of the bleed line and a flow control device in fluid communication with the bleed line.

22. The method of claim 20, wherein the velocity of the fluid in the bleed line is adjusted in response to a sensed velocity in the bleed line.

23. The method of claim 20, further comprising:
determining an amount of dissolved gas in the fluid flowing through the process line as a difference between a gas volume fraction of the fluid flowing through the process line and the total gas content of the fluid flowing through the process line.

24. The method of claim 20, further comprising:
sensing acoustic pressure disturbances in the fluid flowing through the bleed line at different axial locations along the bleed line to provide signals indicative of the sensed acoustic pressure disturbances; and
using the signals indicative of the sensed acoustic pressure disturbances to determine the speed of sound propagating through the fluid flowing through the bleed line.

25. The method of claim 20, wherein the predetermined velocity is at least five times greater than an estimated bubble velocity.

* * * * *